(12) United States Patent
Eastwood et al.

(10) Patent No.: US 7,919,325 B2
(45) Date of Patent: Apr. 5, 2011

(54) METHOD AND APPARATUS FOR MONITORING LIQUID FOR THE PRESENCE OF AN ADDITIVE

(75) Inventors: Ian M. Eastwood, Rossendale (GB);
Erwin Dorland, York (GB);
Mohammed Salem Al-Jafari, York (GB); David M. Goodall, York (GB);
Edmund T. Bergstrom, York (GB)

(73) Assignee: Authentix, Inc., Addison, TX (US)

( * ) Notice: Subject to any disclaimer, the term of this patent is extended or adjusted under 35 U.S.C. 154(b) by 2081 days.

(21) Appl. No.: 10/852,336

(22) Filed: May 24, 2004

(65) Prior Publication Data
US 2005/0260764 A1    Nov. 24, 2005

(51) Int. Cl.
*G01N 21/64* (2006.01)
*G01N 21/76* (2006.01)
(52) U.S. Cl. .......................................... 436/56; 436/172
(58) Field of Classification Search ............... 436/56, 436/172
See application file for complete search history.

(56) References Cited

U.S. PATENT DOCUMENTS

| | | |
|---|---|---|
| 3,973,134 A | 8/1976 | Begley et al. |
| 4,077,719 A | 3/1978 | Barrett et al. |
| 4,084,100 A | 4/1978 | Begley et al. |
| 4,194,170 A | 3/1980 | Kurnit |
| 4,195,930 A | 4/1980 | Delhaye et al. |
| 4,209,690 A | 6/1980 | Rentzepis |
| 4,218,628 A | 8/1980 | Harris |
| 4,277,760 A | 7/1981 | Eckbreth |
| 4,284,354 A | 8/1981 | Liao |
| 4,399,539 A | 8/1983 | White |
| 4,405,237 A | 9/1983 | Manuccia et al. |
| 4,441,943 A | 4/1984 | Kydd |
| 4,486,884 A | 12/1984 | White |
| 4,488,308 A | 12/1984 | McClain |
| 4,500,995 A | 2/1985 | White |
| 4,504,949 A | 3/1985 | White |
| 4,512,660 A | 4/1985 | Goldberg |

(Continued)

FOREIGN PATENT DOCUMENTS

DE          2410033 B1    1/1975

(Continued)

OTHER PUBLICATIONS

Arkles, Barry; "Silane Coupling Agent Chemistry;" The British Library, pp. 59-64.

(Continued)

*Primary Examiner* — Krishnan S Menon
*Assistant Examiner* — Rebecca Fritchman
(74) *Attorney, Agent, or Firm* — Kelly Kordzik; Matheson Keys Garsson & Kordzik PLLC

(57) ABSTRACT

The present invention relates to an apparatus and methods for the identification or authentication of liquid products by the addition of an anti-Stokes marker. The invention features an apparatus and method for the identification of a liquid, dynamic or static, that includes adding an anti-Stokes luminescent marker compound to the liquid followed by exposing the compound to a light source of a known wavelength or known wavelengths and then detecting one or more shorter wavelength emissions from the marker, where the identity of the liquid is confirmed by the emission wavelength or wavelengths that are detected and quantified. The irradiating source of light includes, but is not limited to, a laser and other conventional light sources.

50 Claims, 6 Drawing Sheets

U.S. PATENT DOCUMENTS

| | | | |
|---|---|---|---|
| 4,538,274 A | 8/1985 | George |
| 4,555,176 A | 11/1985 | Moore et al. |
| 4,570,081 A | 2/1986 | Baldwin |
| 4,573,792 A | 3/1986 | Kajiyama et al. |
| 4,580,267 A | 4/1986 | White |
| 4,620,284 A | 10/1986 | Schnell et al. |
| 4,628,513 A | 12/1986 | White |
| 4,758,081 A | 7/1988 | Barnes |
| 4,767,219 A | 8/1988 | Bibby |
| 4,770,853 A | 9/1988 | Bernstein |
| 4,784,450 A | 11/1988 | Jain et al. |
| 4,784,486 A | 11/1988 | Van Wagenen et al. |
| 4,823,166 A | 4/1989 | Hartog et al. |
| 4,867,518 A | 9/1989 | Stamitz et al. |
| H742 H | 2/1990 | Bobbs et al. |
| 5,037,200 A | 8/1991 | Kodama |
| 5,043,265 A | 8/1991 | Tanke et al. |
| 5,054,935 A | 10/1991 | Tanabe et al. |
| 5,071,416 A | 12/1991 | Heller et al. |
| 5,102,232 A | 4/1992 | Tanabe et al. |
| 5,113,277 A | 5/1992 | Ozawa et al. |
| 5,206,699 A | 4/1993 | Stewart et al. |
| 5,217,306 A | 6/1993 | Wada |
| 5,232,124 A | 8/1993 | Schneider et al. |
| 5,262,644 A | 11/1993 | Maguire |
| 5,272,334 A | 12/1993 | Sai |
| 5,303,710 A | 4/1994 | Bashkansky et al. |
| 5,323,404 A | 6/1994 | Grubb |
| 5,351,117 A | 9/1994 | Stewart et al. |
| 5,413,839 A | 5/1995 | Chatwin et al. |
| 5,429,952 A | 7/1995 | Garner et al. |
| 5,432,631 A | 7/1995 | Mamyshev |
| 5,449,233 A | 9/1995 | Sai et al. |
| 5,458,595 A | 10/1995 | Tadir et al. |
| 5,473,458 A | 12/1995 | Mamyshev et al. |
| 5,525,516 A | 6/1996 | Krutak et al. |
| 5,592,282 A | 1/1997 | Hartog |
| 5,618,108 A | 4/1997 | Sai et al. |
| 5,628,410 A | 5/1997 | Smith et al. |
| 5,639,162 A | 6/1997 | Sai |
| 5,696,778 A | 12/1997 | MacPherson |
| 5,696,863 A | 12/1997 | Kleinerman |
| 5,710,046 A | 1/1998 | Rutledge et al. |
| 5,723,338 A | 3/1998 | Rutledge et al. |
| 5,753,449 A | 5/1998 | Yamaguchi et al. |
| 5,753,511 A | 5/1998 | Selinfreund |
| 5,755,512 A | 5/1998 | White |
| 5,765,948 A | 6/1998 | Sai |
| 5,786,893 A | 7/1998 | Fink et al. |
| 5,800,576 A | 9/1998 | Johnson et al. |
| 5,804,447 A | 9/1998 | Albert et al. |
| 5,814,468 A | 9/1998 | Siiman et al. |
| 5,820,265 A | 10/1998 | Kleinerman |
| 5,825,804 A | 10/1998 | Sai |
| 5,828,450 A | 10/1998 | Dou et al. |
| 5,830,763 A | 11/1998 | Junk et al. |
| 5,837,357 A | 11/1998 | Matsuo et al. |
| 5,841,545 A | 11/1998 | Young |
| 5,843,783 A | 12/1998 | Rutledge et al. |
| 5,850,623 A | 12/1998 | Carman, Jr. et al. |
| 5,866,430 A | 2/1999 | Grow |
| 5,870,188 A | 2/1999 | Ozaki et al. |
| 5,876,121 A | 3/1999 | Burns et al. |
| 5,881,083 A | 3/1999 | Diaz-Garcia et al. |
| 5,891,738 A | 4/1999 | Soini et al. |
| 5,928,222 A | 7/1999 | Kleinerman |
| 5,928,954 A | 7/1999 | Rutledge et al. |
| 5,942,444 A | 8/1999 | Rittenburg et al. |
| 5,946,090 A | 8/1999 | Tashiro et al. |
| 5,953,477 A | 9/1999 | Wach et al. |
| 5,956,131 A | 9/1999 | Mamyshev et al. |
| 5,958,780 A | 9/1999 | Asher et al. |
| 5,959,296 A | 9/1999 | Cyr et al. |
| 5,963,680 A | 10/1999 | Kleinerman |
| 5,984,983 A | 11/1999 | Asgaonkar et al. |
| 5,990,197 A | 11/1999 | Escano et al. |
| 5,991,479 A | 11/1999 | Kleinerman |
| 5,997,590 A | 12/1999 | Johnson et al. |
| 5,998,211 A | 12/1999 | Albert et al. |
| 6,011,615 A | 1/2000 | Mamyshev et al. |
| 6,036,885 A | 3/2000 | Krutak, Sr. et al. |
| 6,039,894 A | 3/2000 | Sanjurjo et al. |
| 6,040,191 A | 3/2000 | Grow |
| 6,044,285 A | 3/2000 | Chaiken et al. |
| 6,061,134 A | 5/2000 | Jensen et al. |
| 6,067,154 A | 5/2000 | Hossain et al. |
| 6,070,093 A | 5/2000 | Oosta et al. |
| 6,072,615 A | 6/2000 | Mamyshev |
| 6,099,930 A | 8/2000 | Cyr et al. |
| 6,108,081 A | 8/2000 | Holtom et al. |
| 6,122,042 A | 9/2000 | Wunderman et al. |
| 6,138,913 A | 10/2000 | Cyr et al. |
| 6,141,090 A | 10/2000 | Mamyshev et al. |
| 6,144,791 A | 11/2000 | Wach et al. |
| 6,151,155 A | 11/2000 | Durfee, III et al. |
| 6,159,686 A | 12/2000 | Kardos et al. |
| 6,174,400 B1 | 1/2001 | Krutak, Sr. et al. |
| 6,174,424 B1 | 1/2001 | Wach et al. |
| 6,217,794 B1 | 4/2001 | Neal et al. |
| 6,222,970 B1 | 4/2001 | Wach et al. |
| 6,229,503 B1 | 5/2001 | Mays, Jr. et al. |
| 6,266,211 B1 | 7/2001 | Thomas, III et al. |
| 6,267,913 B1 | 7/2001 | Marder et al. |
| 6,274,381 B1 | 8/2001 | Pauls et al. |
| 6,275,205 B1 | 8/2001 | Winer |
| 6,275,285 B1 | 8/2001 | Nottke et al. |
| 6,285,446 B1 | 9/2001 | Farhadiroushan |
| 6,297,018 B1 | 10/2001 | French et al. |
| 6,307,624 B1 | 10/2001 | Bruck et al. |
| 6,307,626 B1 | 10/2001 | Miles et al. |
| 6,312,914 B1 | 11/2001 | Kardos et al. |
| 6,312,958 B1 * | 11/2001 | Meyer et al. .................... 436/56 |
| 6,313,423 B1 | 11/2001 | Sommer et al. |
| 6,322,909 B1 | 11/2001 | Sakaguchi |
| 6,359,745 B1 | 3/2002 | Thomas, III et al. |
| 6,366,726 B1 | 4/2002 | Wach et al. |
| 6,370,406 B1 | 4/2002 | Wach et al. |
| 6,373,869 B1 | 4/2002 | Jacob |
| 6,377,828 B1 | 4/2002 | Chaiken et al. |
| 6,393,906 B1 | 5/2002 | Vityk et al. |
| 6,416,234 B1 | 7/2002 | Wach et al. |
| 6,432,715 B1 | 8/2002 | Nelson et al. |
| 6,462,863 B1 | 10/2002 | Atieh et al. |
| 6,483,633 B2 | 11/2002 | Onishi et al. |
| 6,485,703 B1 | 11/2002 | Cote et al. |
| 6,487,349 B2 | 11/2002 | Wach et al. |
| 6,490,030 B1 | 12/2002 | Gill et al. |
| 6,498,801 B1 | 12/2002 | Dudelzak et al. |
| 6,509,566 B1 | 1/2003 | Wamsley et al. |
| 6,512,580 B1 | 1/2003 | Behringer et al. |
| 6,514,617 B1 | 2/2003 | Hubbard et al. |
| 6,535,328 B2 | 3/2003 | Yao |
| 6,549,702 B2 | 4/2003 | Islam |
| 6,555,807 B2 | 4/2003 | Clayton |
| 6,574,037 B2 | 6/2003 | Islam |
| 6,580,499 B2 | 6/2003 | Aoki et al. |
| 6,580,500 B2 | 6/2003 | Aoki et al. |
| 6,590,647 B2 | 7/2003 | Stephenson |
| 6,594,005 B2 | 7/2003 | Aoki et al. |
| 6,597,493 B2 | 7/2003 | Islam |
| 6,600,592 B2 | 7/2003 | Islam |
| 6,603,910 B2 | 8/2003 | Islam |
| 6,606,148 B2 | 8/2003 | Fredin et al. |
| 6,608,670 B2 | 8/2003 | Nottke |
| 6,610,351 B2 | 8/2003 | Shchegolikhin et al. |
| 6,643,603 B2 | 11/2003 | Aoki et al. |
| 6,653,652 B2 | 11/2003 | Yasuda et al. |
| 6,661,509 B2 | 12/2003 | Deck |
| 6,686,074 B2 | 2/2004 | Muth |
| 6,693,737 B2 | 2/2004 | Islam |
| 6,760,148 B2 | 7/2004 | Islam |
| 6,781,690 B2 | 8/2004 | Armstrong |
| 2001/0053521 A1 | 12/2001 | Kreimer |
| 2002/0002336 A1 | 1/2002 | Marchitto |
| 2002/0028011 A1 | 3/2002 | Yasuda et al. |
| 2002/0034357 A1 | 3/2002 | Desthieux |
| 2002/0044781 A1 | 4/2002 | Creasey |

| | | |
|---|---|---|
| 2002/0045190 A1 | 4/2002 | Wilson |
| 2002/0045268 A1 | 4/2002 | Lakowicz |
| 2002/0061363 A1 | 5/2002 | Halas |
| 2002/0101579 A1 | 8/2002 | Aoki et al. |
| 2002/0105722 A1 | 8/2002 | Bewersdorf |
| 2002/0109100 A1 | 8/2002 | Jackson |
| 2002/0118712 A1 | 8/2002 | Usuki et al. |
| 2002/0119485 A1 | 8/2002 | Morgan |
| 2002/0122171 A1 | 9/2002 | Aoki et al. |
| 2002/0130304 A1 | 9/2002 | Paeschke |
| 2002/0131618 A1 | 9/2002 | Ahlers |
| 2002/0132045 A1 | 9/2002 | Halas |
| 2002/0132371 A1 | 9/2002 | Kreimer |
| 2002/0133080 A1 | 9/2002 | Apruzzese |
| 2002/0142480 A1 | 10/2002 | Natan |
| 2002/0145385 A1 | 10/2002 | Perlo |
| 2002/0150938 A1 | 10/2002 | Kneipp |
| 2002/0151041 A1 | 10/2002 | Kreimer |
| 2002/0163483 A1 | 11/2002 | Crist |
| 2002/0167692 A1 | 11/2002 | Cunningham et al. |
| 2002/0179828 A1 | 12/2002 | Engelhardt et al. |
| 2002/0185634 A1 | 12/2002 | Marder |
| 2002/0194494 A1 | 12/2002 | Egger et al. |
| 2002/0198928 A1 | 12/2002 | Bukshpan et al. |
| 2003/0007145 A1 | 1/2003 | Shimada et al. |
| 2003/0011765 A1 | 1/2003 | Xie |
| 2003/0016438 A1 | 1/2003 | Islam |
| 2003/0022105 A1 | 1/2003 | Prasad et al. |
| 2003/0026900 A1 | 2/2003 | Weimer |
| 2003/0030067 A1 | 2/2003 | Chen |
| 2003/0030800 A1 | 2/2003 | Golden |

FOREIGN PATENT DOCUMENTS

| | | |
|---|---|---|
| DE | 4224301 A1 | 1/1994 |
| EP | 1241242 A2 | 8/2002 |
| GB | 2209831 B | 5/1990 |
| GB | 2234588 B | 7/1991 |
| WO | WO8706383 | 10/1987 |

OTHER PUBLICATIONS

Aubin, J.E.; "Autofluorescence of Viable Cultured Mammalian Cells;" The Journal of Histochemistry and Cytochemistry; vol. 27, No. 1, pp. 36-43, 1979.

Beverloo, H.B.; "Preparation and Microscopic Visualization of Multicolor Luminescent Immunophosphors;" Wiley-Liss, Inc., Cytometry 13, pp. 561-570, 1992.

Hirao, K.; UV and Blue Upconversion in Tm3+-doped Fluoroaluminate Glass by 0.655 um Excitation; Journal of Non-Crystalline Solids 135 , pp. 90-93, 1991.

Jongkind, J.F.; "Isolation of Autofluorescent 'Aged' Human Fibroblasts by Flow Sorting;" Experimental Cell Research, vol. 138, No. 2, pp. 409-417, 1982.

Jouart, J.P.; "Upconversion in Er3+-doped Fluorite-Type Crystals Pumped by 1.5 um Tunable Duide Laser;" Journal of Luminescence 46, pp. 39-45, 1990.

Kano, Tsuyoshi; "NaLnF4Yb3+,Er3+(Ln:Y,Gd,La): Efficient Green-Emitting Infrared-Excited Phosphors;" Central Research Laboratory of Hitachi Ltd., pp. 1561-1564.

Kelley, Marian M.; "Chlorsulfuron Determination in Soil Extracts by Enzyme Immunoassay:" Journal of Agricultural and Food Chemistry 33, pp. 962-965, 1985.

Koch, M.E.; "Photon Avalanche Upconversion Laser at 644 nm;" Appl. Phys. Lett. 56, pp. 1083-1085, 1990.

Lenth, W.; "Excitation Mechanisms for Upconversion Lasers;" Journal of Luminescence 45, pp. 346-350, 1990.

Limoges, Benoit; "Redox Cationic or Procationic Labeled Drugs Detected at a Perfluorsulfonated Ionomer Film-Coated Electrode;" Journal of Electroanalytical Chemistry 402, pp. 175-187, 1996.

McFarlane, R.A.; "High-Power Visible Upconversion Laser;" Optics Letters, vol. 16, No. 18, pp. 1397-1399, 1991.

MacFarlane, R.M.; "Violet cw Neodymium Upconversion Laser;" Appl. Phys. Lett. 52, pp. 1300-1302, 1988.

McPherson, Gary L.; "Intense Up-Conversion Luminescence Resulting From the Two-Photon Absorption of Er3+ Ions in Crystals of CsMgC13;" Chemical Physics Letter, vol. 179, No. 4, pp. 325-328, 1991.

Monroe, Dan; "Enzyme Immunoassay;" Analytical Chemistry, vol. 56, No. 8, pp. 920a-931a, 1984.

Nederlof, P.M.; "Three-Color Fluorescence in Situ Hybridization for the Simultaneous Detection of Multiple Nucleic Acid Sequences;" Alan R. Liss, Inc., Cytometry 10, pp. 20-27, 1989.

Newsome, William H.; "An Enzyme-Linked Immunosorbent Assay for Metalaxyl in Foods;" J. Agric. Food Chem. 33, pp. 528-530, 1985.

Ni, H.; "Avalanche Upconversion in Tm:YALO3;" Optics Letters, vol. 16, No. 18, pp. 1424-1426, 1991.

Oomen, E.W.J.L.; "On the Origin of the Red Emission Band From Erbium Doped Fluoride Glasses Excited with 800 nm;" Journal of Luminescence 46, pp. 353-358, 1990.

Ploem, M.D., J.S.; "A Study of Filters and Light Sources in Immunofluorescence Microscopy;" Annals of the New York Academy of Sciences, vol. 177, pp. 414-429, 1971.

Silversmith, A.J.; "Green Infrared-Pumped Erbium Upconversion Laser;" Appl. Phys. Lett. 51, pp. 1977-1979, 1987.

Titus, Julie A.; "Texas Red, A Hydrophilic, Red-Emitting Fluorophore for use with Fluorescein in Dual Parameter Flow Microfluormetric and Fluorescence Microscopic Studies;" Journal of Immunological Methods, vol. 50, No. 2, pp. 193-204, 1982.

Van Uitert, L.G.; "Infra-Red Stimulable Rare Earth Oxy-Halide Phosphors; Their Synthesis, Properties and Applications;" Mat. Res. Bull., vol. 4, pp. 381-389, 1969.

Wie, Siong I.; "Development of Enzyme-Linked Immunosorbent Assays for Residue Analysis of Diflubenzuron and BAY SIR 8514;" Journal of Agricultural and Food Chemistry 30, pp. 949-957, 1982.

Wittke, J.P.; "Y2O3:Yb:Er-New Red-Emitting Infrared-Excited Phosphor;" J. Appl. Phys., vol. 43, No. 2, pp. 595-600, 1972.

Yocom, P.N.; "Rare-Earth-Doped Oxysulfides for GaAs-Pumped Luminescent Devices:" Metallurgical Transactions, vol. 2, No. 3, pp. 763-767, 1971.

* cited by examiner

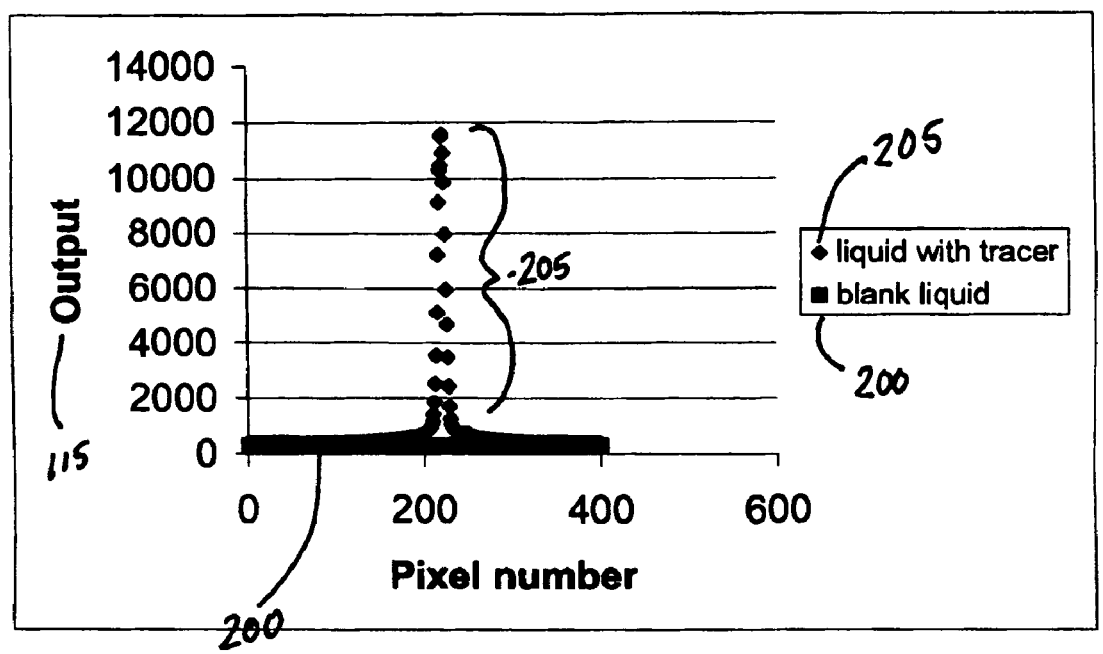

FIGS. 3A through 3D
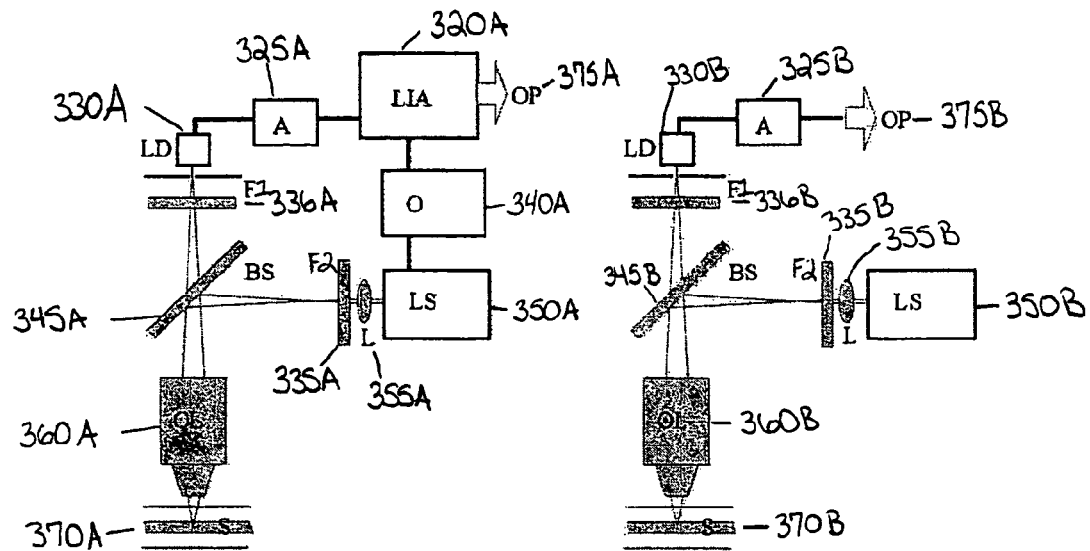
Fig. 3A
Fig. 3B
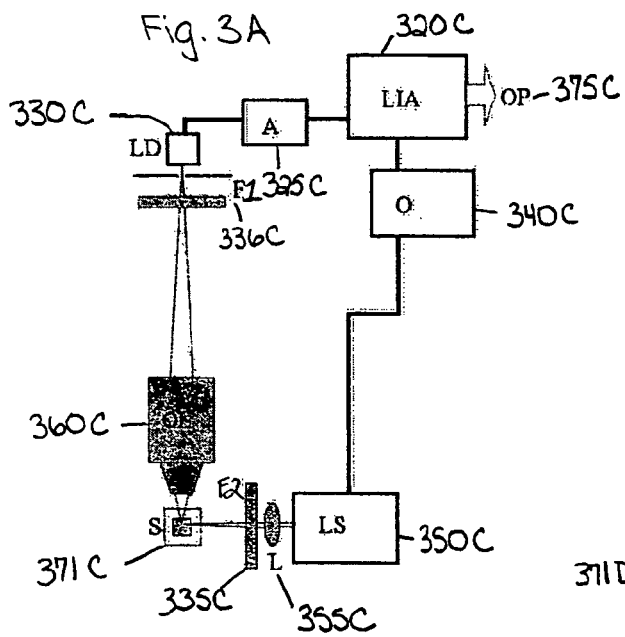
Fig. 3C
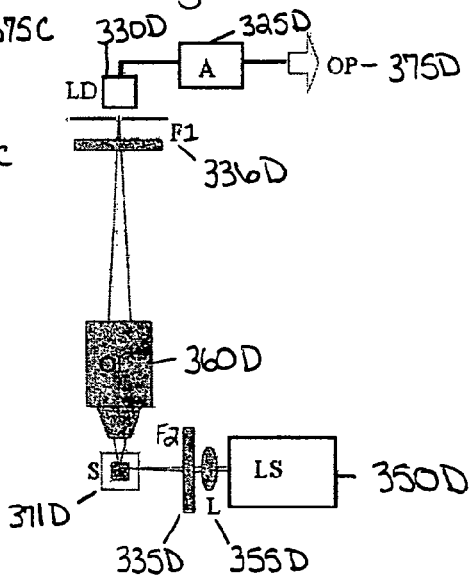
Fig. 3D FIGS. 4A through 4D
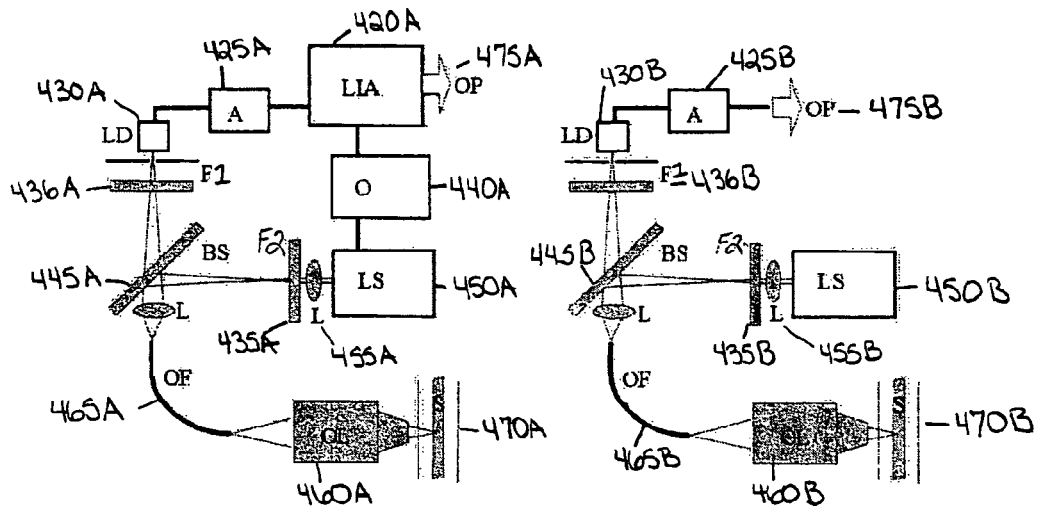
Fig. 4A
Fig. 4B
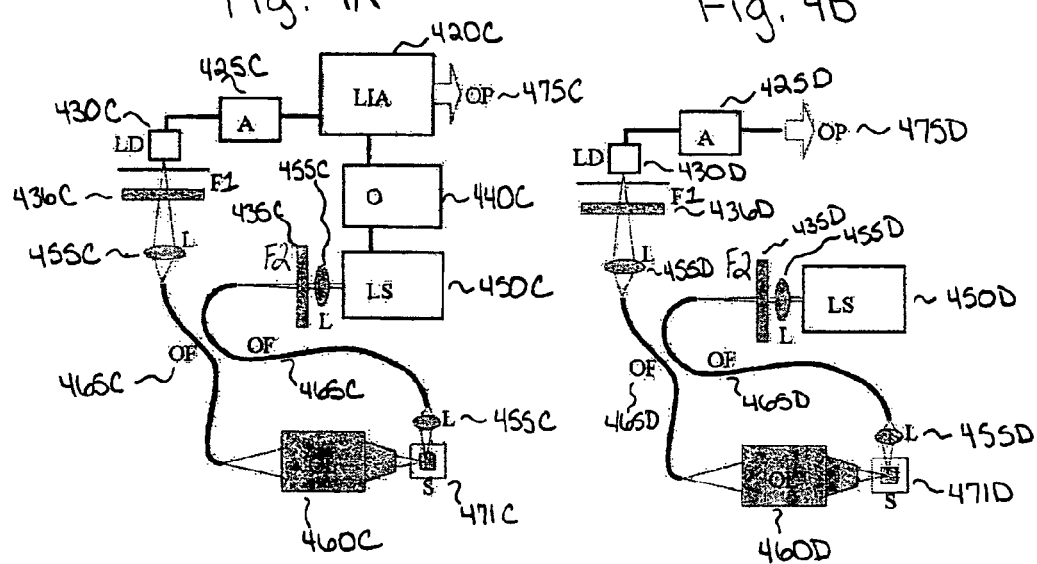
Fig. 4C
Fig. 4D

METHOD AND APPARATUS FOR MONITORING LIQUID FOR THE PRESENCE OF AN ADDITIVE

FIELD OF THE INVENTION

This invention relates to the monitoring of levels of chemical marker compounds. In particular, this invention relates to the monitoring of levels of chemical marker compounds in liquid products and to anti-Stokes emissions.

BACKGROUND OF THE INVENTION

In many areas of the world, major problems are encountered concerning product counterfeiting, unauthorized distribution and sale of products (e.g. grey market trading, parallel trading, product diversion), as well as false liability based on product substitution.

In addition to product counterfeiting, product adulteration is another major problem. Product adulteration takes place when a product is tampered with, such as by dilution. An example of such a problem lies in the adulteration of lubricating oils, or other oil-based products, by addition of a counterfeiter's oil to a genuine product. Such adulteration is not only financially damaging to the oil manufacturer but the consequent lowering of performance which can occur can cause damage to the consumer and consequently harm the reputation of the genuine product.

It is known that various liquid products can be marked using colorants or covert systems in order to make their misuse impossible or at least traceable. Such marking can, for example, trace the identity of liquids, identify various grades, or distinguish manufacturer's brands. Various problems have on occasion accompanied the use of dyes or colorants as markers for liquid products.

In order to detect the presence of a covert marker, many of the existing markers must be extracted by a chemical process. Chemical detection normally requires extraction of the marker with an acidic or basic aqueous liquid extractant, followed by addition of a reagent to cause the extract to turn a visibly distinct colour, although in some cases, the reagent is unnecessary. While effective, this procedure has some drawbacks. For instance, it is time-consuming to perform and often does not provide a good quantitative measurement of marker concentration in field tests.

Some covert markers are organic molecules which either absorb or fluoresce in the near infrared to mark their presence in a liquid sample. U.S. Pat. No. 5,525,516 (Eastman Chemical) and German Patent DE4224301A1 (BASF) describe such markers. While the detection procedure is much simpler, some liquids naturally contain compounds that interfere with the spectrophotometric measurements, potentially compromising accurate quantitative detection.

Detection methods which employ fluorescent labels are of limited sensitivity for a variety of reasons. First, with conventional fluorophores it is difficult to differentiate between specific fluorescent signals and nonspecific background signals. Most common fluorophores are aromatic organic molecules that have broad absorption and emission spectra, with the emission maximum red-shifted 50-100 nm to a longer wavelength than the excitation (i.e., absorption) wavelength. Typically, both the absorption and emission bands are located in the UV/visible portion of the spectrum. The lifetime of the fluorescence emission is generally short, on the order of 1 to 100 ns. These general characteristics of organic dye fluorescence are also applicable to background signals, to which other naturally occurring molecules may contribute, or the sample itself (Jongkind, et al., *Exp. Cell Res.* 138:409, 1982; Aubin, J. E., *J. Histochem. Cytochem.* 27:36, 1979). Therefore, the limit of detection of specific fluorescent signal from typical fluorophores is limited by the significant background noise contributed by nonspecific fluorescence and reflected excitation light.

A second problem of organic dye fluorophores that limits sensitivity is photolytic decomposition of the dye molecule (i.e., photobleaching). Thus, even in situations where background noise is relatively low, it is often not possible to integrate a weak fluorescent signal over a long detection time, since the dye molecules decompose as a function of incident irradiation in the UV and near-UV bands.

A third problem of organic dye fluorophores is that quantitation of the emission is limited due to quenching. For example, energy that is normally released as light energy can be absorbed by intermolecular collisions with the solvent. The amount of quenching experienced by a fluorophore in a liquid sample is highly variable, and can depend on a number of factors, such as temperature, solvent, and possible energy absorbing contaminants in the solvent. As a result, unless the solvent and conditions are highly controlled, true quantitation is difficult to achieve.

When a phosphor or other luminescent material emits light, in general, it emits light according to Stokes' Law, which states that the wavelength of emitted light is always longer than the wavelength of the exciting radiation. While Stokes' Law holds for the majority of cases, it does not hold in all instances. For example, in some cases, the wavelength is the same for both the absorbed and the emitted radiation. That is, the efficiency appears to be perfect or unity. This is known as resonance radiation. Stokes' Law also does not hold when the energy emitted is greater than the energy absorbed, with the emitted light known as an anti-Stokes emission. Anti-Stokes materials typically absorb infrared or near infrared radiation in the range of about 700 to about 1500 nm, and emit light in the near infrared red or visible spectrum. The use of anti-Stokes materials in security documents (for example, European Patent EP 1241242—Bundesdruckerei), and for the authentication of polymers (Hubbard, et al., U.S. Pat. No. 6,514,617), has been described. However, the use of such materials for the identification and/or authentication of liquids has not been described.

SUMMARY

The present invention relates to methods for the identification or authentication of liquid products by the addition of an anti-Stokes marker. The ability to do so could potentially check product counterfeiting, unauthorized distribution and sale of a product, as well as false liability based on product substitution. Because, to our knowledge, anti-Stokes phenomena do not normally exist in nature, liquid samples will not produce light in the region of interest and therefore, will not cause background interference when excited by infrared light. An advantage of this "unnatural" detection system is that non-specific background signals are minimized. Accordingly, the accurate detection of liquids which have an anti-Stokes marker added allows the presence or absence of adulterants to easily be recognised, even if the composition of the liquid changes due to, for example, degradation, or if the precise composition of the liquid is not known. Another advantage is that anti-Stokes markers are more difficult to counterfeit than markers that are currently in use for the identification/authentication of liquids.

Accordingly, a first aspect of the invention features a method for the identification of a liquid, e.g., a petroleum product, that includes adding an anti-Stokes luminescent marker compound to the liquid followed by exposing the compound to a light source of a known wavelength or known wavelengths and then detecting one or more shorter wavelength emissions from the marker, where the identity of the liquid is confirmed by the emission wavelength or wavelengths that are detected.

By "anti-Stokes marker" is meant a substance that, when exposed to an electromagnetic radiation source, emits an electromagnetic radiation signal at a shorter wavelength than that of the source. An anti-Stokes substance can also be referred to as one that is "up-converting." An example of a luminescent compound anti-Stokes marker is one that, when exposed to light with a wavelength of 980 nm emits a light signal at 685 nm. Preferred luminescent compounds are phosphorescent anti-Stokes markers that absorb at least two photons at an excitation frequency and subsequently emit electromagnetic energy at an emission frequency higher (i.e., with a shorter wavelength) than the excitation frequency. Thus, there is an anti-Stokes shift between the original excitation frequency and the final emission frequency.

The marker can be present in the liquid that is marked at concentrations of less than or equal to 10 parts per million. Desirably, the marker is present at a concentration of less than or equal to 1 part per million, and most desirably, less than or equal to 0.1 part per million. In one embodiment, the liquid can include more than one marker, with the liquid subjected to more than one non-overlapping irradiating wavelength and with each marker emitting light of a shorter wavelength than that which it absorbs.

The irradiating source of light can be a laser or other conventional light source, and the irradiation wavelength or wavelength range can be within the visible/IR wavelength range of from 300 nm to 1800 nm, desirably within the IR wavelength range of from 900 nm to 1100 nm or within the range of 1500 nm to 1600 nm. Most desirable is an irradiation wavelength from 960 nm to 985 nm. The anti-Stokes radiation that is detected concurrently or subsequently to irradiation can be within the range of 300 nm to 1800 nm, desirably within the visible/near-IR range of 300 nm to 699 nm or within the near-IR range of 700 nm to 1050 nm.

Certain anti-Stokes markers can be excited by two wavelengths. In one example, the first excitation wavelength is from 300 nm to 1050 nm, preferably from 700 nm to 1050 nm, whilst the second excitation wavelength is from 1050 nm to 1800 nm, preferably from 1500 nm to 1800 nm.

Multiple anti-Stokes luminescent compounds can be used to identify the liquid. In one embodiment, the liquid contains more than one anti-Stokes compound and is exposed to each of a first and a second wavelength of electromagnetic radiation. Two different emissions, each of which is shorter than the wavelength used for the excitation of compound from which they are derived, are then detected and the liquid thereby identified. The first or the second wavelength can be 300 nm to 1800 nm, with the second wavelength not within the wavelength of the first electromagnetic radiation. Preferably, both non-overlapping wavelengths are 800 nm to 1800 nm. In one example, the first wavelength is within the range of 300 nm to 799 nm and the second wavelength is within the range of 800 nm to 1050 nm. In another example, the first wavelength is 900 nm to 1100 nm and the second wavelength is 1500 nm to 1600 nm.

In all of the examples above, the radiation that is emitted can be quantified when it is detected.

Exemplary liquids in which the marker can be used are petroleum products, including, but not limited to, gasoline and diesel; perfumes; water; beverages of all types; agrochemical formulations; bulk liquids; additive packages (e.g. for all fuels and lubricants); and, waste liquids, including, but not limited to, aqueous waste mixtures and organic waste solvents.

The markers can include inorganic lanthanide elements, desirably from one of the following atom groupings: ytterbium and erbium, ytterbium and thulium, ytterbium and holmium, and ytterbium and terbium. The markers can also be organic dyes that give an anti-Stokes emission upon irradiation. The markers can be either dissolved or suspended in the liquid to be identified. If the marker is suspended, the suspension can take the form of a mono-dispersion, a poly-dispersion, an emulsion, or a colloidal mixture. For particulate markers, the particle size can be less than 100 µm, 10 µm, 1 µm, 300 nm, 100 nm, or 10 nm in diameter. Desirably, the particle size is less than 1 µm and, most desirably, less than 300 nm.

In one embodiment, the marker compound is part of a composition that includes a second molecule bound to it. The second molecule can be further functionalized to include binding sites or ligands for other another molecule that is one of two members of a specific binding pair. Cognate pairs can include, for example, an antibody and its ligand, avidin or streptavidin and biotin, or polynucleotides and their complementary nucleotide sequences. Such marker compositions can be removed from the liquid, for example, by affinity chromatography, and subsequently analysed by irradiation and detection of anti-Stokes emission(s), thereby identifying the liquid from which the markers originated.

In another embodiment, the second compound of the composition can increase the solubility of the first marker compound in the liquid. For example, the second compound can include a $C_1$ to $C_{24}$ alkyl group and/or a $C_6$ to $C_{30}$ aryl group, each of which is optionally substituted with from 1 to 6 hydroxy, $C_1$ to $C_6$ ether, $C_3$ to $C_{24}$ polyether, thio, $C_1$ to $C_6$ thioether, amino, $C_1$ to $C_6$ alkylamino, $C_2$ to $C_{12}$ dialkylamino, nitro, carboxy, carboxy-$C_1$ to $C_6$-alkyl, sulfoxy, carboxamido, carbox-$C_1$ to $C_6$-alkylamido, $C_1$ to $C_6$ alkylamido, $C_6$ to $C_{18}$ arylamido, $C_1$ to $C_6$ alkarylamido, $C_1$ to $C_6$ alkylimido, $C_1$ to $C_6$ alkylhydrazido, or $C_6$ to $C_{18}$ arylhydrazido groups to increase the solubility of the first compound. If the marker is suspended in the liquid, the same strategy of using an appropriately functionalized second compound for improving the characteristics of the suspension can be used. Surfactants can be also added to the liquid to improve the characteristics of the suspension (e.g., to prevent aggregation).

The invention encompasses organic and inorganic anti-Stokes markers, but preferably features lanthanide phosphors as markers. Thus, a typical marker of the invention is a sub-micron-size up-converting lanthanide phosphor particle. Another example is a chelated lanthanide ion or a lanthanide ion as part of a cage complex.

By "marker excitation wavelength" is meant an electromagnetic radiation wavelength that, when absorbed by an anti-Stokes marker, produces a detectable fluorescent emission from the anti-Stokes marker, wherein the fluorescent emission is of a shorter wavelength (i.e., higher frequency radiation) than the marker excitation wavelength.

As used herein, the term "marker emission wavelength" refers to a wavelength that is emitted from an anti-Stokes marker subsequent to, or contemporaneously with, illumination of the anti-Stokes marker with one or more excitation wavelengths; marker emission wavelengths of anti-Stokes markers are shorter (i.e., higher frequency radiation) than the corresponding excitation wavelengths. Both marker excitation wavelengths and marker emission wavelengths are characteristic of individual anti-Stokes marker species, and are readily determined by the performance of simple excitation and emission scans.

As used herein, the terms "alkyl" and the prefix "alk-" are inclusive of both straight chain and branched chain saturated or unsaturated groups, and of cyclic groups, i.e., cycloalkyl and cycloalkenyl groups. Unless otherwise specified, acyclic alkyl groups are from 1 to 24 carbons, more preferably from 1 to 6 carbon atoms, and can further include from 1 to 6 heteroatoms, i.e., O, S, Se, P, and/or N atoms, replacing carbons of the alkyl chain. Cyclic groups can be monocyclic or polycyclic and preferably have from 3 to 8 ring carbon atoms. Exemplary cyclic groups include cyclopropyl, cyclopentyl, cyclohexyl, and adamantyl groups.

By "aryl" is meant a mono- or polycyclic carbocyclic aromatic ring or ring system. Unless otherwise specified, aryl groups are from 6 to 30 carbons, more preferably from 6 to 12 carbons. Examples of aryl groups include phenyl, naphthyl, biphenyl, anthracenyl, fluorenyl, and indenyl groups.

By "heteroaryl" or "heteroaryl group" is meant a mono- or polycyclic aromatic ring or ring system that contains at least one ring hetero-atom (e.g., O, S, Se, P, and N). Unless otherwise specified, heteroaryl groups contain from 1 to 9 carbons. Heteroaryl groups include furanyl, thienyl, pyrrolyl, imidazolyl, pyrazolyl, oxazolyl, isoxazolyl, thiazolyl, isothiazolyl, triazolyl, oxadiazolyl, oxatriazolyl, pyridyl, pyridazyl, pyrimidyl, pyrazyl, triazyl, benzofuranyl, isobenzofuranyl, benzothienyl, indole, indazolyl, indolizinyl, benzisoxazolyl, quinolinyl, isoquinolinyl, cinnolinyl, quinazolinyl, naphthyridinyl, phthalazinyl, phenanthrolinyl, purinyl, and carbazolyl groups.

By "heterocycle" or "heterocyclic group" is meant a mono- or polycyclic non-aromatic ring or ring system that contains at least one ring heteroatom (e.g., O, S, Se, P, and N). Unless otherwise specified, heterocyclic groups contain from 2 to 9 carbons. Heterocyclic groups include, for example, dihydropyrrolyl, tetrahydropyrrolyl, piperazinyl, pyranyl, dihydropyranyl, tetrahydropyranyl, dihydrofuranyl, tetrahydrofuranyl, dihydrothiophene, tetrahydrothiophene, and morpholinyl groups.

By "halide" or "halogen" or "halo" is meant bromine, chlorine, iodine, or fluorine.

Aryl, heteroaryl, or heterocyclic groups may be unsubstituted or substituted by one or more substituents selected from the group consisting of $C_{1-6}$ alkyl, hydroxy, halo, nitro, $C_{1-6}$ alkoxy, $C_{1-6}$ alkylthio, trifluoromethyl, $C_{1-6}$ acyl, arylcarbonyl, heteroarylcarbonyl, nitrile, $C_{1-6}$ alkoxycarbonyl, arylalkyl (wherein the alkyl group has from 1 to 6 carbon atoms) and heteroarylalkyl (wherein the alkyl group has from 1 to 6 carbon atoms).

By "polynucleotide" is meant a homo- or heteropolymer of two or more nucleotide units connected by phosphodiester linkages.

By "saccharide" is meant any mono- or polysaccharide. Monosaccharides are polyhydric alcohols from three to ten or more carbon atoms containing ether and aldehyde group (e.g., aldoses) or a keto group (e.g., ketoses), or masked aldehyde or keto groups, or derivatives thereof. Examples of monosaccharides are the D and L configurations of glyceraldehyde, erythrose, threose, ribose, arabinose, xylose, lyxose, allose, altrose, glucose, mannose, gulose, idose, galactose, talose, dihydroxyacetone, erythrulose, ribulose, xylulose, puscose, fructose, sorbose and/or tagatose. Examples of monosaccharides also include those monosaccharide deoxy sugars, such as, for example, fucose, rhamnose, and digitoxose; deoxyamino sugars such as, for example, glucosamine, mannosamine, galactosamine; deoxyacylamino sugars such as, for example, N-acetylglucosamine, N-acetylmannosamine, and N-acetylgalactosamine; and aldonic, aldaric and/or uronic acids such as, for example, gluconic acid or glucuronic acid. Monosaccharides also include ascorbic acid, amino acid-carrying monosaccharides and monosaccharides which carry lipid, phosphatidyl or polyol residues. Saccharides can also include polysaccharides, i.e., any polymer of monosaccharides, or salts therein. Polysaccharides include starch, dextran, cellulose, chitosan, glycogen, hyaluronic acid, alginic acid, and glycosylaminoglycans.

BRIEF DESCRIPTION OF THE DRAWINGS

FIG. 2 is a graphic display of the output measured for a blank sample and a liquid sample containing an anti-Stokes tracer.

FIGS. 3A-3D depict schematic diagrams showing a plurality of apparatus configurations useful with the method of the present invention for the detection of up-converters in dynamic and static samples.

FIGS. 4A-4D depict schematic diagrams showing a plurality of hand-held apparatus configurations useful with the method of the present invention for the detection of up-converters in dynamic and static samples.

DETAILED DESCRIPTION

Figure 1:
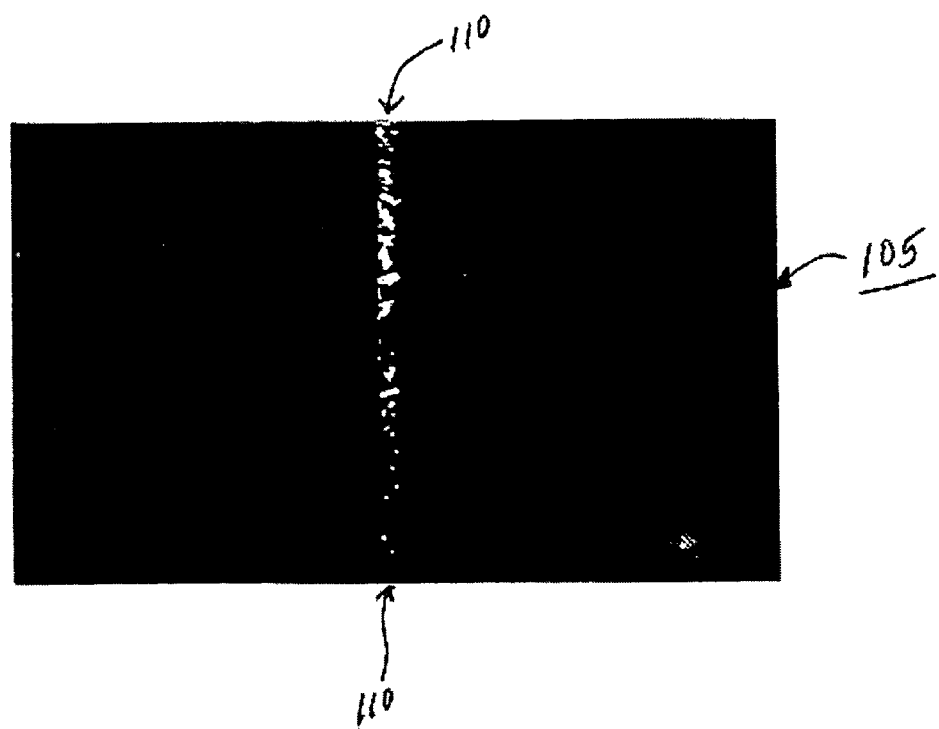
FIG. 1 depicts a liquid containing an anti-Stokes marker and its depiction thereof due to irradiation with a laser beam.

A wide variety of fluorescent dyes that offer a selection of excitation and emission spectra are available for the identification of liquids according to the invention. It is possible to select fluorophores having emission spectra that are sufficiently different so as to permit multitarget detection and discrimination with multiple probes, wherein each probe species is linked to a different fluorophore. Because the spectra of fluorophores can be discriminated on the basis of both narrow band excitation and selective detection of emission spectra, two or more distinct target species can be detected and resolved (Titus, et al., J. Immunol. Methods 50:193 (1982); Nederlof, et al., Cytometry 10:20 (1989); Ploem, J S Ann. N.Y. Acad. Sci. 177:414 (1971)).

The anti-Stokes markers of the invention permit essentially total rejection of non-specific background autofluorescence, and are characterized by excitation and emitted wavelengths that are typically in the infrared or visible portions of the spectrum, respectively. Use of these markers allows conversion of long-wavelength excitation radiation (e.g., near-IR) to emitted radiation at wavelengths shorter than the excitation wavelength. Thus, the invention provides for the identification of liquids using luminescent materials that are capable of multiphoton excitation and that have up-shifted emission spectra.

The markers of the invention include anti-Stokes inorganic phosphors and/or anti-Stokes organic dyes. The markers can be attached to various other compounds, such as antibodies, streptavidin, protein A, polypeptide ligands, or polynucleotides. Such marker compositions, in which the molecule that is attached to the marker is one of two members of a specific binding pair, can be removed from the liquid by, for example, affinity chromatography, and subsequently analysed by irradiation and detection of anti-Stokes emission(s), thereby identifying the liquid from which the markers originated.

Attachment of the anti-Stokes marker to other compounds can be accomplished using various known linkage chemistries, depending upon the nature of the specific compound to which the marker is attached. For example, microcrystalline anti-Stokes lanthanide phosphor particles may be coated with a polycarboxylic acid (e.g., Additon XW 330, Hoechst, Frankfurt, Germany) during milling and various proteins (e.g., immunoglobulin, streptavidin or protein A) can be physically adsorbed to the surface of the phosphor particle (Beverloo et al., "Preparation and microscopic visualization of multicolor luminescent immunophosphors", Cytometry 13:561-570 (1992), which is incorporated herein by reference).

Alternatively, various inorganic phosphor coating techniques can be employed including, but not limited to: spray drying, plasma deposition, and derivatization with functional groups (e.g., —COOH, —NH$_2$, —CONH$_2$) attached by a silane coupling agent to —SiOH moieties coated on the phosphor particle or incorporated into a vitroceramic phosphor particle comprising silicon oxide(s) and anti-Stokes phosphor compositions. Vitroceramic phosphor particles can be aminated with, for example, aminopropyltriethoxysilane for the purpose of attaching amino groups to the vitroceramic surface on linker molecules. Using this chemical strategy, other omega-functionalized silanes can be substituted for aminopropyltriethoxysilane to attach alternative functional groups. Other molecules, such as proteins or polynucleotides, may then be directly attached to the vitroceramic phosphor by covalent linkage, for example through siloxane bonds or through carbon-carbon bonds to linker molecules (e.g., organofunctional silylating agents) that are covalently bonded to or adsorbed to the surface of a phosphor particle.

Covalent conjugation between the anti-Stokes inorganic phosphor particles and a protein (e.g., avidin or an immunoglobulin) can be accomplished with heterobifunctional crosslinkers. For example, surface silanization of the phosphors with tri(ethoxy)thiopropyl silane leaves a phosphor surface with a thiol functionality to which a protein (e.g., antibody) or any compound containing a primary amine can be grafted using conventional N-succinimidyl(4-iodoacetyl) amino-benzoate chemistry.

Microcrystalline anti-Stokes phosphor particles are typically smaller than 100 microns in diameter, desirably less than 1 micron in diameter (i.e., submicron), and most desirably are 0.1 to 0.3 microns or less in diameter. It is generally most preferred that the phosphor particles are as small as possible while retaining sufficient quantum conversion efficiency to produce a detectable signal.

Anti-Stokes up-conversion has been found to occur in certain materials containing rare-earth ions in certain crystal materials. For example, ytterbium and erbium act as an activator couple in a phosphor host material such as barium-yttrium-fluoride. The ytterbium ions act as the absorber, and transfer energy non-radioactively to excite the erbium ions. The emission is thus characteristic of the erbium ion's energy levels.

Although the invention can be practiced with a variety of anti-Stokes inorganic phosphors, desirable embodiments employ one or more phosphors derived from one of several different phosphor host materials, each doped with at least one activator couple. Suitable phosphor host materials include: sodium yttrium fluoride (NaYF$_4$), lanthanum fluoride (LaF$_3$), lanthanum oxysulfide, yttrium oxysulfide, yttrium fluoride (YF$_3$), yttrium gallate, yttrium aluminum garnet, gadolinium fluoride (GdF$_3$), barium yttrium fluoride (BaYF$_5$, BaY$_2$F$_8$), and gadolinium oxysulfide. Suitable activator couples are selected from: ytterbium/erbium, ytterbium/thulium, and ytterbium/holmium. Other activator couples suitable for up-conversion may also be used. By combination of these host materials with the activator couples, at least three phosphors with at least three different emission spectra (red, green, and blue visible light) are possible. Generally, the absorber is ytterbium and the emitting center can be selected from: erbium, holmium, terbium, and thulium; however, other anti-Stokes phosphors of the invention may contain other absorbers and/or emitters. The molar ratio of absorber:emitting center is typically at least about 1:1, more usually at least about 3:1 to 5:1, preferably at least about 8:1 to 10:1, more preferably at least about 11:1 to 20:1, and generally less than about 250:1, usually less than about 100:1, and more usually less than about 50:1 to 25:1, although various ratios may be selected on the basis of desired characteristics (e.g., chemical properties, manufacturing efficiency, absorption cross-section, excitation and emission wavelengths, quantum efficiency, or other considerations). The ratio(s) chosen will generally also depend upon the particular absorber-emitter couple(s) selected, and can be calculated from reference values in accordance with the desired characteristics.

The optimum ratio of absorber (e.g., ytterbium) to the emitting center (e.g., erbium, thulium, or holmium) varies, depending upon the specific absorber/emitter couple. For example, the absorber:emitter ratio for Yb:Er couples is typically in the range of about 20:1 to about 100:1, whereas the absorber:emitter ratio for Yb:Tm and Yb:Ho couples is typically in the range of about 500:1 to about 2000:1. These different ratios are attributable to the different matching energy levels of the Er, Tm, or Ho with respect to the Yb level in the crystal. For most applications, anti-Stokes phosphors may conveniently comprise about 10-30% Yb and either: about 1-2% Er, about 0.1-0.05% Ho, or about 0.1-0.05% Tm, although other formulations may be employed.

Some embodiments of the invention feature inorganic phosphors that are excited by infrared radiation of about 950 to 1100 nm, preferably about 960 to 985 nm. For example, a microcrystalline inorganic phosphor of the formula YF$_3$:Yb$_{0.10}$Er$_{0.01}$ exhibits a luminescence intensity maximum at an excitation wavelength of about 980 nm. Inorganic phosphors of the invention typically have emission maxima that are in the visible range. For example, specific activator couples have characteristic emission spectra: ytterbium-erbium couples have emission maxima in the red or green portions of the visible spectrum, depending upon the phosphor host; ytterbium-holmium couples generally emit maximally in the green portion, ytterbium-thulium typically have an emission maximum in the blue range, and ytterbium-terbium usually emit maximally in the green range. For example, Y$_{0.80}$Yb$_{0.19}$Er$_{0.01}$F$_2$ emits maximally in the green portion of the spectrum.

Although anti-Stokes inorganic phosphor crystals of various formulae are suitable for use in the invention, the following formulae, provided for example and not to limit the invention, are generally suitable:

Na(Y$_x$Yb$_y$Er$_z$)F$_4$: x is 0.7 to 0.9, y is 0.09 to 0.29, and z is 0.05 to 0.01; Na(Y$_x$Yb$_y$Ho$_z$)F$_4$: x is 0.7 to 0.9, y is 0.0995 to 0.2995, and z is 0.0005 to 0.001; Na(Y$_x$Yb$_y$Tm$_z$)F$_4$: x is 0.7 to 0.9, y is 0.0995 to 0.2995, and z is 0.0005 to 0.001; and (Y$_x$Yb$_y$Er$_z$)O$_2$S: x is 0.7 to 0.9, y is 0.05 to 0.12; z is 0.05 to 0.12. In addition, (Y$_{0.86}$Yb$_{0.08}$Er$_{0.06}$)$_2$O$_3$ is a relatively efficient anti-Stokes phosphor material.

For example, ytterbium(Yb)-erbium(Er)-doped yttrium oxysulfides luminesce in the green after excitation at 950 nm.

These are non-linear phosphors, in that the ytterbium acts as an "antenna" (absorber) for two 950 nm photons and transfers its energy to erbium, which acts as an emitter (activator). The critical grain size of the phosphor is given by the quantum yield for green emission and the doping level of both Yb and Er, which is generally in the range of about 1 to 10 percent, more usually in the range of about 2 to 5 percent. A typical Yb:Er phosphor crystal comprises about 10-30% Yb and about 1-2% Er. Thus, a phosphor grain containing several thousand formula units ensures the emission of at least one or more photons during a typical laser irradiation time. However, the nonlinear relationship between absorption and emission indicates that intense illumination at the excitation wavelength(s) may be necessary to obtain satisfactory signal in embodiments employing very small phosphor particles (i.e., less than about 0.3 µm). Additionally, it is desirable to increase the doping levels of activator/emitter couples for producing very small phosphor particles so as to maximize quantum conversion efficiency.

In certain applications, such as where highly sensitive detection is required, intense illumination can be provided by commercially available sources, such as infrared laser sources (e.g., continuous wave (CW) or pulsed semiconductor laser diodes). For example, in applications where the microcrystalline phosphor particle must be very small and the quantum conversion efficiency is low, intense laser illumination can increase signal and decrease detection times. Alternatively, some embodiments of the invention employ phosphor compositions that have inherently low quantum conversion efficiencies (e.g., low doping levels of activator couple), but which have other desirable characteristics (e.g., manufacturing efficiency, ease of derivatization, etc.); such low efficiency anti-Stokes phosphors are preferably excited with laser illumination at a frequency at or near (i.e., within about 25 to 75 µm) an absorption maximum of the material. The fact that no other light is generated in the system other than from the anti-Stokes phosphor allows for extremely sensitive signal detection, particularly when intense laser illumination is used as the source of excitation radiation. Thus, the unique property of up-conversion of photon energy by anti-Stokes phosphors makes possible the detection of very small particles of microcrystalline inorganic phosphors.

For example, various phosphor material compositions capable of up-conversion are suitable for uses in the invention are shown in Table I.

In addition to the materials shown in Table I and variations thereof, aluminates, phosphates, and vanadates can be suitable phosphor host materials. In general, when silicates are used as a host material, the conversion efficiency is relatively low. In certain uses, hybrid anti-Stokes phosphor crystals may be made (e.g., combining one or more host material and/or one or more absorber ion and/or one or more emitter ion).

Exemplary anti-Stokes phosphors excited at about 980 nm include, but are not limited to: $(Y_{0.80}Yb_{0.18}Er_{0.02})F_3$; $(Y_{0.87}Yb_{0.129}Tm_{0.001})F_3$; $(Y_{0.80}Yb_{0.198}Ho_{0.002})F_3$ $(Gd_{0.80}Yb_{0.18}Er_{0.02})F_3$; $(Gd_{0.87}Yb_{0.129}Tm_{0.001})F_3$; $(Gd_{0.80}Yb_{0.198}Ho_{0.002})F_3$; $(Y_{0.86}Yb_{0.08}Er_{0.06})_2O_2S$; $(Y_{0.87}Yb_{0.129}Tm_{0.001})_2O_2S$; $(Y_{0.08}Yb_{0.198}Ho_{0.002})_2O_2S$; $(Gd_{0.86}Yb_{0.08}Er_{0.06})_2O_2S$; $(Gd_{0.87}Yb_{0.129}Tm_{0.001})_2O_2S$; $(Gd_{0.80}Yb_{0.198}Ho_{0.002})_2O_2S$.

Exemplary Anti-Stokes phosphors excited at about 1500 nm include, but are not limited to: $(Y_{0.96}Er_{0.04})_2O_2S$ and $(Gd_{0.96}Er_{0.04})_2O_2S$.

TABLE I

| Host Material | Phosphor Material Compositions | | |
|---|---|---|---|
| | Absorber Ion | Emitter Ion | Color |
| Oxysulfides ($O_2S$) | | | |
| $Y_2O_2S$ | Ytterbium | Erbium | Green |
| $Gd_2O_2S$ | Ytterbium | Erbium | Red |
| $La_2O_2S$ | Ytterbium | Holmium | Green |
| Oxyhalides ($OX_y$) | | | |
| YOF | Ytterbium | Thulium | Blue |
| $Y_3OCl_7$ | Ytterbium | Terbium | Green |
| Fluorides ($F_x$) | | | |
| $YF_3$ | Ytterbium | Erbium | Red |
| $GdF_3$ | Ytterbium | Erbium | Green |
| $LaF_3$ | Ytterbium | Holmium | Green |
| $NaYF_3$ | Ytterbium | Thulium | Blue |
| $BaYF_5$ | Ytterbium | Thulium | Blue |
| $BaY_2F_8$ | Ytterbium | Terbium | Green |
| Gallates ($Ga_xO_y$) | | | |
| $YGaO_3$ | Ytterbium | Erbium | Red |
| $Y_3Ga_5O_{12}$ | Ytterbium | Erbium | Green |
| Silicates ($Si_xO_y$) | | | |
| $YSi_2O_5$ | Ytterbium | Holmium | Green |
| $Ysi_3O_7$ | Ytterbium | Thulium | Blue |

Techniques and methods for manufacture of inorganic phosphors have been described in the art. Anti-Stokes phosphor crystals can be manufactured by those of ordinary skill in the art by various published methods, including but not limited to the following: Yocom et al., Metallurgical Transactions 2:763 (1971); Kano et al., J. Electrochem. Soc., p. 1561 (1972); Wittke et al., J. Appl. Physics 43:595 (1972); Van Uitert et al., Mat. Res. Bull. 4:381 (1969); which are incorporated herein by reference. Other references which may be referred to are: Jouart J P and Mary G J. Luminescence 46:39 (1990); McPherson G L and Meyerson S L Chem. Phys. Lett. (April) p. 325 (1991); Oomen et al., J. Luminescence 46:353 (1990); NI H and Rand S C Optics Lett. 16 (September) (1991); McFarlane R A Optics Lett. 16 (September) (1991); Koch et al., Appl. Phys. Lett. 56:1083 (1990); Silversmith et al., Appl. Phys. Lett. 51:1977 (1987); Lenth W and McFarlane R M J. Luminescence 45:346 (1990); Hirao et al., J. Non-crystalline Solids 135:90 (1991); and McFarlane et al., Appl. Phys. Lett. 52:1300 (1988), which are incorporated herein by reference.

In general, inorganic phosphor particles are milled to a desired average particle size and distribution by conventional milling methods known in the art, including milling in a conventional barrel mill with zirconia and/or alumina balls for periods of up to about 48 hours or longer. Phosphor particles used in binding assays are typically 3.0 to 0.001 µm in diameter (or along the long axis if non-spherical), more preferably 2.0 to 0.1 µm in size, and most preferably 1.0 to 0.3 µm in size, although phosphor particles larger or smaller than these dimensions may be used. Fractions having a particular particle size range may be prepared by sedimentation, generally over an extended period (i.e., a day or more) with removal of the desired size range fraction after the appropriate sedimentation time. The sedimentation process may be monitored, such as with a Horiba Particle Analyzer.

Milling crystalline materials is not always optimal. With milling, the particle morphology is not uniform, as milled particles result from the random fracture of larger crystalline particles. Since the sensitivity of a detection assay using anti-Stokes inorganic phosphors depends on the ability to distinguish between bound and unbound phosphor particles, it is preferable that the particles be closer to identical size and morphology. Size, weight, and morphology of anti-Stokes microcrystalline phosphor particles can affect the number of potential binding sites per particle and thus the potential strength of particle binding to reporter and/or analyte. Monodisperse submicron spherical particles of uniform size can be generated by homogeneous precipitation reactions at high dilutions. For example, small yttrium hydroxy carbonate particles are formed by the hydrolysis of urea in a dilute yttrium solution. Similarly, anti-Stokes inorganic phosphors can be prepared by homogeneous precipitation reactions in dilute conditions. For example, $(Y_{0.86}Yb_{0.08}Er_{0.06})_2O_3$ was prepared as monodispersed spherical particles in the submicron size range by precipitation.

After precipitation it is typically necessary to anneal the oxide in air at about 1500.degree. C., which can cause faceting of the spherical particles and, subsequently, generation of aggregates. Faceting can be reduced by converting the small spherical particles of the oxide or hydroxy carbonate precursor to the oxysulfide phase by including a polysulfide flux for annealing. Using this technique, efficient oxysulfide particles in the 0.3 to 0.4 µm diameter range are prepared as a dispersion in water. Sonication can be used to produce a monodisperse mixture of discrete spherical particles. After fractionation and coating, these particles can be used as anti-Stokes markers. This general preparative procedure is suitable for preparing smaller phosphor particles (e.g., 0.1 µm diameter or smaller).

Frequently, such as with phosphors having an oxysulfide host material, the phosphor particles can be dispersed in a polar solvent, such as acetone or DMSO, to generate a substantially monodisperse emulsion (e.g., for a stock solution). Aliquots of the monodisperse stock solution may be further diluted with an organic or an aqueous solvent (e.g., a solution of avidin in buffered water or buffered saline).

Washing phosphors in acetone or DMSO improves the suspendability of inorganic phosphor particles in water. Phosphor particles prepared with polysulfide flux are preferably resuspended and washed in hot DMSO and heated for about an hour in a steam bath then allowed to cool to room temperature under continuous agitation. The phosphor particles may be pre-washed with acetone (typically heated to boiling) prior to placing the particles in the DMSO. Hot DMSO-treated phosphors were found to be reasonably hydrophilic and form stable suspensions. A Microfluidizer™ (Microfluidics Corp.) can be used to further improve the dispersion of particles in the mixture. DMSO-phosphor suspensions can be easily mixed with water, preferably with small amounts of surfactant present. In general, polysaccharides (e.g., guar gum, xanthan gum, gum arabic, alginate, guaiac gum) can be used to promote deaggregation of particles. Particles can be washed in hot DMSO and serially diluted into a 0.1% aqueous gum arabic solution, which almost completely eliminates water dispersion problems of phosphors. Resuspended phosphors in an organic solvent, such as DMSO, are allowed to settle for a suitable period (e.g., about 1-3 days), and the supernatant, which is typically turbid, is used for subsequent conjugation.

Ludox™ is a colloidal silica dispersion in water with a small amount of organic material (e.g., formaldehyde, glycols) and a small amount of alkali metal. Ludox™ and its equivalents can be used to coat anti-Stokes phosphor particles, which can subsequently be fired to form a ceramic silica coating which cannot be removed from the phosphor particles, but which can be readily silanized with organofunctional silanes (containing thiol, primary amine, and carboxylic acid functionalities) using standard silanization chemistries (Arkles, B, in: Silicon Compounds: Register and Review; 5th Edition (1991); Anderson, R G, Larson, G L, and Smith, C, eds.; p. 59-64, Huls America, Piscataway, N.J.).

Phosphor particles can be coated or treated with surface-active agents (e.g., anionic surfactants such as Aerosol OT) during the milling process or after milling is completed. For example, particles may be coated with a polycarboxylic acid (e.g., Additon XW 330, Hoechst, Frankfurt, Germany or Tamol, see Beverloo et al. (1992) op.cit.) during milling to produce a stable aqueous suspension of phosphor particles, typically at pH 6-8. The pH of an aqueous solution of phosphor particles can be adjusted by addition of a suitable buffer and titration with acid or base to the desired pH range. Depending upon the chemical nature of the coating, some minor loss in conversion efficiency of the phosphor may occur as a result of coating. However, the power available in a laser excitation source can compensate for such reduction in conversion efficiency and ensure adequate phosphor emission.

In general, preparation of inorganic phosphor particles and linkage to binding reagents is performed essentially as described in Beverloo et al. (1992) op.cit. or in U.S. Pat. No. 5,043,265. Alternatively, a water-insoluble polyfunctional polymer which exhibits glass and melt transition temperatures well above room temperature can be used to coat the anti-Stokes phosphors in a nonaqueous medium. For example, such polymer functionalities include: carboxylic acids (e.g., 5% aminoethyl acrylate/95% methyl acrylate copolymer), reducible sulfonates (e.g., 5% sulfonated polystyrene), and aldehydes (e.g, polysaccharide copolymers) the phosphor particles are coated with water-insoluble polyfunctional polymers by coacervative encapsulation in nonaqueous media, washed, and transferred to a suitable aqueous buffer solution to conduct the heterobifunctional crosslinking to a protein (e.g., antibody) or a polynucleotide. An advantage of using water-insoluble polymers to coat phosphors for their use in aqueous liquids is that the polymer microcapsule will not migrate from the surface of the phosphor upon storing the encapsulated phosphors in an aqueous solution (i.e., improved reagent stability). Another advantage in using copolymers in which the encapsulating polymer is only partially functionalized is that one can control the degree of functionalization, and thus the number of biological molecules which can be attached to a phosphor particle, on average. Since the solubility and encapsulation process depends on the dominant nonfunctionalized component of the copolymer, the functionalized copolymer ratio can be varied to generate a range of potential crosslinking sites per phosphor, without having to substantially change the encapsulation process.

A preferred functionalization method employs heterobifunctional crosslinkers that links the biological macromolecule probe to the insoluble phosphor particle in three steps: (1) bind the crosslinker to the polymer coating on the phosphor, (2) separate the unbound crosslinker from the coated phosphors, and (3) bind the biological macromolecule to the washed, linked polymer-coated phosphor. This method reduces undesirable crosslinking interactions between biological macromolecules and so reduces irreversible aggregation as described in U.S. Pat. No. 5,043,265.

In some embodiments of the invention, a liquid can contain an anti-Stokes marker compound that is bound to a second compound, such as an immunoglobulin, a polynucleotide, streptavidin, Protein A, a receptor ligand, or another bifunctional molecule that contains a binding moiety or a ligand. In one example, covalent conjugation between proteins (e.g., avidin, immunoglobulin, etc.) and anti-Stokes inorganic phosphor particles or anti-Stokes organic dyes can be accomplished with heterobifunctional crosslinkers. Liquids containing such functionalized markers can be subjected to an affinity purification step such as, for example, affinity chromatography, followed by isolation of a marker-cognate mixture. This mixture can then be irradiated at a suitable wavelength and the detection of an anti-Stokes emission used to identify the liquid from which the marker was isolated. More than one marker-cognate pairing can be used for liquid identification.

In other embodiments, a liquid can contain an anti-Stokes marker composition that includes an organic compound adsorbed to an inorganic anti-Stokes phosphor crystal and/or covalently attached to a coated inorganic anti-Stokes phosphor, a derivatized vitroceramic anti-Stokes phosphor, or a microencapsulated anti-Stokes phosphor. The organic compound of the composition may be functionalized with one or more groups selected from the following: a substituted or unsubstituted $C_1$ to $C_{24}$ linear or branched alkyl group; a substituted or unsubstituted $C_6$ to $C_{30}$ aryl group; a substituted or unsubstituted $C_1$ to $C_6$ alkaryl group; or a substituted or unsubstituted heteroaryl group. Substituents for these groups can be selected from one to four halo, hydroxy, $C_1$ to $C_6$ ether, $C_3$ to $C_{24}$ polyether, thio, $C_1$ to $C_6$ thioether, amino, $C_1$ to $C_6$ alkylamino, $C_2$ to $C_{12}$ dialkylamino, nitro, carboxy, carboxy-$C_1$ to $C_6$-alkyl, sulfoxy, carboxamido, carbox-$C_1$ to $C_6$-alkylamido, $C_1$ to $C_6$ alkylamido, $C_6$ to $C_{18}$ arylamido, $C_1$ to $C_6$ alkarylamido, $C_1$ to $C_6$ alkylimido, $C_1$ to $C_6$ alkylhydrazido, and $C_6$ to $C_{18}$ arylhydrazido groups. The marker also can be an anti-Stokes organic dye, which can be further conjugated with other organic molecules with useful binding or solubilizing functionality as described above for the inorganic markers. Examples of organic anti-Stokes dyes can be found in U.S. Patent Application 20030022105 A1, which is hereby incorporated by reference.

Referring to FIG. 1, a sample 105 containing a liquid is shown, wherein the sample was measured by an excitation Laser light source by introducing the light source from shoot-through top to bottom aspect, wherein the sample 105 measured contains an anti-Stoke tracer 110. After the excitation Laser light source encountered the liquid sample 105, light was emitted from the phosphor reporters contained within the sample 105. The sample 105 of FIG. 1 can then be measured utilizing at least one of the configurations as described in FIGS. 3, 4 and 5.

As will be described in greater detail below, an output 115, depicted in FIG. 2, is generated from a sample that is measured and represents the intensity of light in the emission band which provides the amount of reporter (anti-Stoke tracer 110) present in the sample. This resultant output is used in quantitation of dilution or other characteristics of the sample measured.

Specifically, FIG. 2 depicts an example of an output 115 of the comparison of measured liquid samples 200, 205, wherein liquid sample 200 represents a sample of a liquid that does not contain an anti-Stokes tracer but liquid sample 205 does contain the anti-Stokes tracer. It is evident from FIG. 2 that quantitation of the sample 205 measured is readily achieved by use of an anti-Stokes tracer within the liquid. FIG. 2 depicts the experimental results from Example 1, later described.

Figure 5:
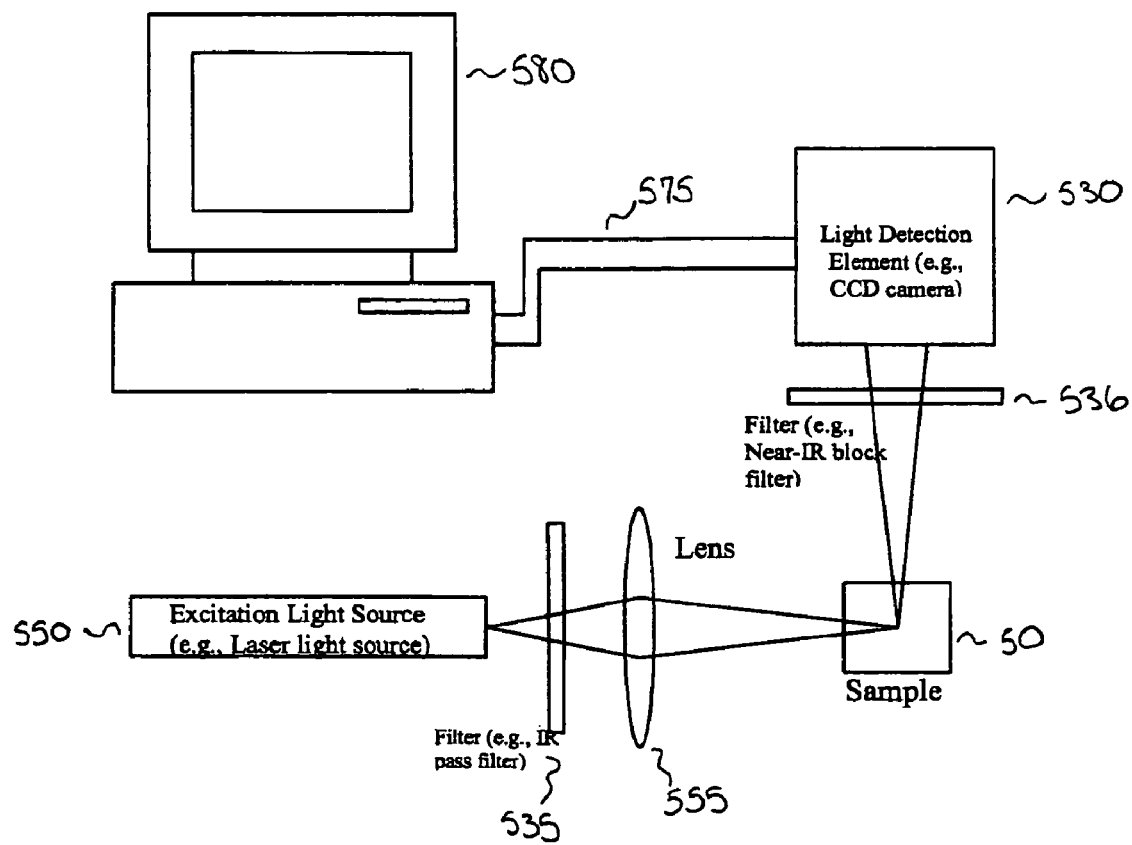
FIG. 5 is a diagram depiction of the physical configuration of the apparatus utilized to test the samples of Examples 1, 2, and 3 herein.

The nature of the present invention provides considerable flexibility in the selection of various apparatus configurations used for carrying out the methods disclosed herein. FIGS. 3, 4 and 5 show schematic diagrams showing a plurality of configurations used with the method of the present invention for the detection of up-converter markers. The abbreviations used within these figures depict the following: a LIA, lock-in amplifier; A, amplifier; LD, light detecting element (e.g. photodiode, avalanche photodiode, photomultiplier tube, photodiode array or CCD); F1, IR pass spectral and spatial filters; F2, near IR cutting/block filters; O, oscillator; BS, beamsplitter; LS, excitation light source (e.g. laser diode, LED); L, lens; OL, objective lens (e.g. microscope objective or fibre coupler); OF, optical fiber; S, sample; and, an OP, output.

The following product and part number listings are provided merely to give a complete understanding of the various types of components used in FIGS. 3A-3D, FIGS. 4A-4D and FIG. 5. It should be understood that these components are not meant to limit one skilled in the art to only these specific products for use in the invention disclosed herein.

Examples of an excitation light source (LS) include, but are not limited to, a laser module (e.g., Roithner Lasertechnik, Vienna, Austria part No C2021-B1), a light emitting diode (E.g., Maplin Electronics South Yorkshire, UK part No LD271), a lamp (E.g., Ocean Optics, The Netherlands part No DH-2000-DUV) or focussed and filtered natural light.

Examples of lenses (L) include, but are not limited to Lambda Research Optics Inc, California, USA Part No BCX-10B-050 or Edmond Optics Ltd, York, UK, Part No. C45-155.

Examples of beam splitters/mirrors (BS) include, but are not limited to, Edmond Optics Ltd, York, UK, Part No. C43-843.

Examples of objective lenses (OL) used to carry out the method comprise, but are not limited to, Edmond Optics Ltd, York, UK, Part No. C46-406.

Examples of light detecting elements (LD) available to carry out the method comprise, but are not limited to, CCD device e.g., an Astrocam camera, Cambridge, UK, part No 4201-TE4/A fitted with EEV 05-10 CCD chip 298×1152 pixels 22.5 µm square, a photo multiplier tube e.g., Hamamatsu Photonics UK Ltd, Hertfordshire, UK, Part No H3164-10, a photo diode e.g., Hamamatsu Photonics UK Ltd, Hertfordshire, UK, Part No G8376-01, an avalanche photodiode e.g., Hamamatsu Photonics UK Ltd, Hertfordshire, UK, Part No S2381 or a photodiode array e.g., Hamamatsu Photonics UK Ltd, Hertfordshire, UK, Part No S2721-02.

Examples of filters F1 and F2 used include, but are not limited to, e.g., Edmond Optics Ltd, York, UK, Catalog No. C46-151 or Lambda Research Optics Inc, California, USA Part No BG-18-12.7.

Examples of specific amplifiers (A) available to carry out the method include, but are not limited to, RS Components Ltd, Northants, UK part No. 203-215 or 296-9787

Examples of lock-in amplifiers (LIA) available to carry out the method include, but are not limited to, Edmond Optics Ltd, York, UK, Catalog No. C55-784

An example of an oscillator (O) available to carry out the method includes, but is not limited to, a TTI function generator—part number TG210, Thurlby Thandar Instruments Ltd., Huntingdon, Cambridgeshire, UK.

It should be emphasized that the configurations depicted in FIGS. 3A-D, 4A-D and 5, that will be described hereinbelow, are examples of implementations of configurations used for the detection of up-converter markers in both dynamic samples (e.g., a pipeline) and static samples (e.g., a test tube) and merely are set forth for providing a clearer understanding of the principles of the method of the invention disclosed herein. Many variations to the devices will be apparent to persons skilled in the art upon reference to the description. A plurality of variations may be made to the configurations of the apparatus without departing from the spirit and principles used to carry out the methods of the invention.

Generally speaking, detection and quantitation of an anti-Stokes substance is accomplished by illuminating a sample suspected of containing up-converting phosphors with electromagnetic radiation at an excitation wavelength and then detecting phosphorescent radiation. Illumination of the sample is produced by exposing the sample (e.g., dynamic or static) to electromagnetic radiation produced by at least one excitation light source (LS). Various excitation light sources (LS) may be used, including infrared laser diodes and LEDs, as well as other suitable sources. Optical filters (F) which can have high transmissibility in the excitation wavelength range and low transmissibility in one or more undesirable wavelength bands can be employed to filter out undesirable wavelengths from the excitation source illumination. Undesirable wavelength ranges are potential sources of background noise from scattered excitation illumination.

Excitation illumination may also be multiplexed and/or collimated. For example, beams of various discrete frequencies from multiple coherent sources (e.g., lasers) can be collimated and multiplexed using an array of beam splitters/mirrors (BS). In this way, samples containing multiple phosphor species having different excitation wavelength bands can be illuminated at their excitation frequencies simultaneously. Illumination may be continuous or pulsed, or may combine continuous wave (CW) and pulsed illumination where multiple illumination beams are multiplexed (e.g., a pulsed beam is multiplexed with a CW beam), permitting signal discrimination between phosphorescence induced by the CW source and phosphorescence induced by the pulsed source, thus allowing the discrimination of multiple phosphor species having similar emission spectra but different excitation spectra.

Schematic illustrations of the first four of at least eight embodiments of an apparatus which are used to implement the method of the invention are shown in FIGS. 3A-3D.

Specifically referring now to FIG. 3A, in the case of a single reporter in a dynamic sample, a sample 370A containing molecules which are to be imaged for determination of anti-Stokes markers is illuminated by at least one excitation light source (LS) 350A. An excitation light source (LS) 350A capable of emitting light at one or more wavelengths in the reporter's excitation band and a detector that is sensitive to at least some wavelengths in the reporter's emission band is utilized. The light source (LS) 350A may be derived from any convenient light source including, but not limited to, inexpensive near-infrared laser diodes or light-emitting diodes (LEDs).

The excitation light source (LS) 350A is directed through lens 355A into filter 335A to filter out undesirable wavelengths from the excitation light source 350A illumination. Specifically, filter 335A is adapted to permit the transmission of excitation wavelengths while blocking emission wavelengths. As previously stated, undesirable wavelength ranges are potential sources of background noise resulting from scattered excitation light source 350A illumination.

If further reference to FIG. 3A, the excitation illumination light proceeding out of filter 335A may also be multiplexed and/or collimated using an array of beam splitters/mirrors 345A.

Light from source 350A that is reflected by the beam splitter/mirrors (BS) 345A is then focused by an objective lens (OL) 360A or other focusing mechanism, wherein the focused light thereby encounters the dynamic sample (S) 370A.

After the excitation source light encounters the dynamic sample (S) 370A, light is thereby emitted by the phosphor reporters contained within the sample (S) 370A. Light is then directed to a light detecting element (LD) 330A such as a photodiode, avalanched photodiode, photomultiplier tube, photodiode array, or charged coupled device (CCD). Depending on the detector's 330A spectral response, it may be necessary to provide filter 336A such as, but not limited to, spectral filters and spatial filters to filter the excitation light. More specifically, filter 336A is adapted to allow the transmission of emission wavelengths while blocking illumination wavelengths. The signal received from the light detecting element (LD) 330A is then fed into an amplifier 325A for increasing the power of the signal received from the light detecting element (LD) 330A.

The amplified signal is then directed through a lock-in amplifier (LIA) 320A to measure the amplitude and phase of signals that are buried in background noise. Lock-in amplifiers (LIA) 320A achieve this by acting as a narrow bandpass filter which removes much of the unwanted background noise while allowing through the signal which is to be quantified. In addition, an oscillator (O) 340A is connected to the lock-in amplifier (LIA) 320A and the light source (LS) 350A for generating the AC signal for producing output (OP) 375A.

An electrical signal is output (OP) 375A representing the intensity of light in the emission band which provides the amount of reporter present which is used in quantitation of dilution or other characteristics of the dynamic sample (S) 370A.

Now specifically referring to FIG. 3B, in the case of a single reporter in a dynamic sample, a sample 370B containing molecules which are to be imaged for determination of anti-Stokes markers is illuminated by at least one excitation light source (LS) 350B. An excitation light source (LS) 350B capable of emitting light at one or more wavelengths in the reporter's excitation band and a detector that is sensitive to at least some wavelengths in the reporter's emission band is utilized. The light source (LS) 350B may be derived from any convenient light source including, but not limited to, inexpensive near-infrared laser diodes or light-emitting diodes (LEDs).

The excitation light source (LS) 350B is then directed through a lens 355B into a filter 335B to filter out undesirable wavelengths from the excitation light source 350B illuminations. Specifically, filter 335B is adapted to permit the transmission of excitation wavelengths while blocking emission wavelengths. As previously stated, undesirable wavelength ranges are potential sources of background noise resulting from scattered excitation light source 350B illumination.

If further reference to FIG. 3B, the excitation illumination light proceeding out of filter 335B may also be multiplexed and/or collimated using an array of beam splitters/mirrors 345B. Light from source (LS) 350B that is reflected by the beam splitter/mirrors (BS) 345B is then focused by an objective lens (OL) 360B or other focusing mechanism, wherein the focused light thereafter encounters a dynamic sample (S) 370B.

After the excitation source light encounters the dynamic sample (S) 370B, light is thereby emitted by the phosphor reporters contained within the dynamic sample (S) 370B. Light is then directed to a light detecting element (LD) 330B such as a photodiode, avalanched photodiode, photomultiplier tube, photodiode array, or charged coupled device (CCD). Depending on the detector's 330B spectral response, it may be necessary to provide a filter 336B such as, including but not limited to, a spectral filters and spatial filters to filter the excitation light before entering the light detecting element (LD) 330B. The signal received from the light detecting element (LD) 330B is then fed into an amplifier 325B for increasing the power of the signal received from the light detecting element (LD) 330B.

An electrical signal is output (OP) 375B representing the intensity of light in the emission band which provides the amount of reporter present which is used in quantitation of dilution or other characteristics of the dynamic sample (S) 370B.

Now in specific reference to FIG. 3C, in the case of a single reporter in a static sample 371C (e.g., a test tube) containing molecules which are to be imaged for determination of anti-Stokes markers is illuminated by at least one excitation light source (LS) 350C. An excitation light source (LS) 350C capable of emitting light at one or more wavelengths in the reporter's excitation band and a detector that is sensitive to at least some wavelengths in the reporter's emission band is utilized. The light source (LS) 350C may be derived from any convenient light source including, but not limited to, inexpensive near-infrared laser diodes or light-emitting diodes (LEDs).

The excitation light source (LS) 350C is then directed through a lens (L) 355C into a filter 335C to filter out undesirable wavelengths from the excitation light source 350C illumination. Specifically, filter 335C is adapted to permit the transmission of excitation wavelengths while blocking emission wavelengths. As previously stated, undesirable wavelength ranges are potential sources of background noise resulting from scattered excitation light source 350C illumination.

Light filtered by filter (F) 335C is then directed to and encounters static sample (S) 371C. After the excitation source light encounters the static sample (S) 371C, light is thereby emitted by the phosphor reporters contained within the static sample (S) 371C and is directed to and focused through an objective lens (OL) 360C.

Light coming from objective lens (OL) 360C is then directed to a light detecting element (LD) 330C such as a photodiode, avalanched photodiode, photomultiplier tube, photodiode array, or charged coupled device (CCD). Depending upon the detector's 330C spectral response, it may be necessary to provide a filter 336C, such as, but not limited to, spectral filters and spatial filters to filter the excitation light. More specifically, filter 336C is adapted to allow the transmission of emission wavelengths while blocking illumination wavelengths. The signal received from the light detecting element (LD) 330C is then fed into an amplifier 325C for increasing the power of the signal received from the light detecting element (LD) 330C.

The amplified light signal is then directed through a lock-in amplifier (LIA) 320C to measure the amplitude and phase of signals that are buried in background noise. Lock-in amplifiers (LIA) 320C achieve this by acting as a narrow bandpass filter which removes much of the unwanted background noise while allowing through the signal which is to be quantified. In addition, an oscillator (O) 340C is connected to the lock-in amplifier (LIA) 320C and the light source (LS) 350C for generating the AC signal for producing output (OP) 375C.

An electrical signal is output (OP) 375C representing the intensity of light in the emission band which provides the amount of reporter present which is used in quantitation of dilution or other characteristics of the static sample (S) 371C.

Now referring to FIG. 3D, in the case of a single reporter in a static sample 371D (e.g., a test tube) containing molecules which are to be imaged for determination of anti-Stokes markers is illuminated by at least one excitation light source (LS) 350D. An excitation light source (LS) 350D capable of emitting light at one or more wavelengths in the reporter's excitation band and a detector that is sensitive to at least some wavelengths in the reporter's emission band is utilized. The light source (LS) 350D may be derived from any convenient light source including, but not limited to, inexpensive near-infrared laser diodes or light-emitting diodes (LEDs).

The excitation light source (LS) 350D is then directed through a lens (L) 355D into a filter 335D to filter out undesirable wavelengths from the excitation light source (LS) 350D illumination. Specifically, filter 335D is adapted to permit the transmission of excitation wavelengths while blocking emission wavelengths. As previously stated, undesirable wavelength ranges are potential sources of background noise resulting from scattered excitation light source (LS) 350D illumination.

Light filtered by filter (F) 335D is then directed to and encounters static sample (S) 371D. After the excitation source light encounters the static sample (S) 371D, light is thereby emitted by the phosphor reporters contained within the static sample (S) 371D and is directed to and focused through an objective lens (OL) 360D. Light coming from objective lens (OL) 360D is then directed to a light detecting element (LD) 330D such as a photodiode, avalanched photodiode, photomultiplier tube, photodiode array, or charged coupled device (CCD). Depending on the detector's (LD) 330D spectral response, it may be necessary to provide a filter (F) 336D, such as, but not limited to, spectral filters and spatial filters to filter the excitation light.

Next, the signal received from the light detecting element (LD) 330D is then fed into an amplifier (A) 325D for increasing the power of the signal received from the light detecting element (LD) 330D. An electrical signal is then output (OP) 375D representing the intensity of light in the emission band which provides the amount of reporter present which is used in quantitation of dilution or other characteristics of the static sample (S) 370D.

In general reference to FIGS. 4A-4D is shown a schematic view of the optical arrangement of additional embodiments of an apparatus for carrying out the method of the present invention on dynamic and static samples using a hand-held probe or the like. These embodiments can be used in the form of a miniaturized instrument comprising a housing (not shown) and a hand-held probe (not shown) with an optical fiber connecting cable. The optical and electronics components can be, but are required to be, located within the housing.

Now referring to FIG. 4A, is depicted in the case of a single reporter in a dynamic sample, a dynamic sample 470A containing molecules which are to be imaged for determination of anti-Stokes markers is illuminated by at least one excitation light source (LS) 450A. An excitation light source (LS) 450A capable of emitting light at one or more wavelengths in the reporter's excitation band and a detector that is sensitive to at least some wavelengths in the reporter's emission band is utilized. The light source (LS) 450A may be derived from any convenient light source including, but not limited to, inexpensive near-infrared laser diodes or light-emitting diodes (LEDs).

The excitation light source (LS) 450A is then directed through a lens (L) 455A into a filter (F) 435A to filter out undesirable wavelengths from the excitation light source (LS) 450A illumination. Specifically, filter 435A is adapted to permit the transmission of excitation wavelengths while blocking emission wavelengths. As previously stated, undesirable wavelength ranges are potential sources of background noise resulting from scattered excitation light source (LS) 450A illumination.

If further reference to FIG. 4A, the excitation illumination light proceeding out of filter 435A may also be multiplexed and/or collimated using an array of beam splitters/mirrors 445A. Light from source 450A that is reflected by the beam splitter/mirrors (BS) 445A is then focused by lens (L) 455A, wherein the focused light is thereby directed through an optical fiber (OF) 465A to objective lens (OL) 460A. The light departing the objective lens (OL) 460A then encounters dynamic sample (S) 470A.

After the excitation source light encounters the dynamic sample (S) 470A, light is thereby emitted by the phosphor reporters contained within the dynamic sample (S) 470A. The emitted light is thereafter directed back through the objective lens (OL) 460A and through optical fiber 465A to lens (L) 455A.

After passing back through lens (L) 455A the emitted light is directed to a light detecting element (LD) 430A such as a photodiode, avalanched photodiode, photomultiplier tube, photodiode array, or charged coupled device (CCD). Depending on the detector's 430A spectral response, it may be necessary to provide a filter 436A, such as, but not limited to, spectral filters and spatial filters to filter the excitation light before directing it to the light detecting element (LD) 430A. The signal received from the light detecting element (LD) 430A is then fed into an amplifier 425A for increasing the power of the signal received from the light detecting element (LD) 430A.

The amplified signal is then directed through a lock-in amplifier (LIA) 420A to measure the amplitude and phase of signals that are buried in background noise. Lock-in amplifiers (LIA) 420A achieve this by acting as a narrow bandpass filter which removes much of the unwanted background noise while allowing through the signal which is to be quantified. In addition, an oscillator (O) 440A is connected to the lock-in amplifier (LIA) 420A and the light source (LS) 450A for generating the AC signal for producing output (OP) 475A.

The electrical signal output (OP) 475A represents the intensity of light in the emission band which provides the amount of reporter present which is used in quantitation of dilution or other characteristics of the dynamic sample (S) 470A.

Now referring to FIG. 4B, is depicted in the case of a single reporter in a dynamic sample, a sample 470B containing molecules which are to be imaged for determination of anti-Stokes markers is illuminated by at least one excitation light source (LS) 450B. An excitation light source (LS) 450B capable of emitting light at one or more wavelengths in the reporter's excitation band and a detector that is sensitive to at least some wavelengths in the reporter's emission band is utilized. The light source (LS) 450B may be derived from any convenient light source including, but not limited to, inexpensive near-infrared laser diodes or light-emitting diodes (LEDs).

The excitation light source (LS) 450B is directed through a lens (L) 455B into a filter (F) 435B to filter out undesirable wavelengths from the excitation light source (LS) 450B illumination. Specifically, filter 435B is adapted to permit the transmission of excitation wavelengths while blocking emission wavelengths. As previously stated, undesirable wavelength ranges are potential sources of background noise resulting from scattered excitation light source (LS) 450B illumination.

If further reference to FIG. 4B, the excitation illumination light proceeding out of filter 435B may also be multiplexed and/or collimated using an array of beam splitters/mirrors 445B. Light from source 450B that is reflected by the beam splitter/mirrors (BS) 445B is then focused by lens (L) 455B, wherein the focused light is thereby directed through an optical fiber (OF) 165 to objective lens (OL) 460B. The light departing the objective lens (OL) 460B then encounters dynamic sample (S) 470B.

After the excitation source light encounters the dynamic sample (S) 470B, light is thereby emitted by the phosphor reporters contained within the dynamic sample (S) 470B. The emitted light is thereafter directed back through the objective lens (OL) 460B and through optical fiber 165 to lens (L) 455B.

After passing back through lens (L) 455B the emitted light is directed to a light detecting element (LD) 430B such as a photodiode, avalanched photodiode, photomultiplier tube, photodiode array, or charged coupled device (CCD). Depending on the detector's 430B spectral response, it may be necessary to provide a filter 436B, such as, but not limited to, spectral filters and spatial filters to filter the excitation light before directing it to the light detecting element (LD) 430B. More specifically, filter 436B is adapted to allow the transmission of emission wavelengths while blocking illumination wavelengths. The signal received from the light detecting element (LD) 430B is then fed into an amplifier 425B for increasing the power of the signal received from the light detecting element (LD) 430B.

The electrical signal output (OP) 475B represents the intensity of light in the emission band which provides the amount of reporter present which is used in quantitation of dilution or other characteristics of the dynamic sample (S) 470B.

Now referring to FIG. 4C, is depicted in the case of a single reporter in a static sample 471C, a static sample 471C containing molecules which are to be imaged for determination of anti-Stokes markers is illuminated by at least one excitation light source (LS) 450C. An excitation light source (LS) 450C capable of emitting light at one or more wavelengths in the reporter's excitation band and a detector that is sensitive to at least some wavelengths in the reporter's emission band is utilized. The light source (LS) 450C may be derived from any convenient light source including, but not limited to, inexpensive near-infrared laser diodes or light-emitting diodes (LEDs).

The excitation light source (LS) 450C is then directed through a lens (L) 455C into a filter (F) 435C to filter out undesirable wavelengths from the excitation light source (LS) 450C illumination. Specifically, filter 435C is adapted to permit the transmission of excitation wavelengths while blocking emission wavelengths. As previously stated, undesirable wavelength ranges are potential sources of background noise resulting from scattered excitation light source (LS) 450C illumination.

If further reference to FIG. 4C, the excitation illumination light proceeding out of filter 435C from light source 450C is directed through optical fiber (OF) 465C into lens (L) 455C where it is focused upon the static sample (S) 471C. After the excitation source light encounters the static sample (S) 471C, light is thereby emitted by the phosphor reporters contained within the static sample (S) 471C. The emitted light is thereafter directed through an objective lens (OL) 460C into optical fiber 465C to lens (L) 455C, wherein the light is focused and directed to light detecting element (LD) 430C such as a photodiode, avalanched photodiode, photomultiplier tube, photodiode array, or charged coupled device (CCD).

Depending on the detector's 430C spectral response, it may be necessary to provide a filter 436C, such as, but not limited to, spectral filters and spatial filters to filter the excitation light before directing it to the light detecting element (LD) 430C. The signal received from the light detecting element (LD) 430C is then fed into an amplifier 425C for increasing the power of the signal received from the light detecting element (LD) 430C.

The amplified signal is then directed through a lock-in amplifier (LIA) 420C to measure the amplitude and phase of signals that are buried in background noise. Lock-in amplifiers (LIA) 420C achieve this by acting as a narrow bandpass filter which removes much of the unwanted background noise while allowing through the signal which is to be quantified. In addition, an oscillator (O) 440C is connected to the lock-in amplifier (LIA) 420C and the light source (LS) 450C for generating the AC signal for producing output (OP) 475C.

The electrical signal output (OP) 475C represents the intensity of light in the emission band which provides the amount of reporter present which is used in quantitation of dilution or other characteristics of the static sample (S) 471C.

Now referring to FIG. 4D, is depicted in the case of a single reporter in a static sample, a static sample 471D containing molecules which are to be imaged for determination of anti-Stokes markers is illuminated by at least one excitation light source (LS) 450D. An excitation light source (LS) 450D capable of emitting light at one or more wavelengths in the reporter's excitation band and a detector that is sensitive to at least some wavelengths in the reporter's emission band is utilized. The light source (LS) 450D may be derived from any convenient light source including, but not limited to, inexpensive near-infrared laser diodes or light-emitting diodes (LEDs).

The excitation light source (LS) 450D is then directed through a lens (L) 455D into a filter (F) 435D to filter out undesirable wavelengths from the excitation light source (LS) 450D illumination. Specifically, filter 435D is adapted to permit the transmission of excitation wavelengths while blocking emission wavelengths. As previously stated, undesirable wavelength ranges are potential sources of background noise resulting from scattered excitation light source (LS) 450D illumination.

If further reference to FIG. 4D, the excitation illumination light proceeding out of filter 435D from light source 450D is directed through optical fiber (OF) 465D into lens (L) 455D where it is focused upon the static sample (S) 471D. After the excitation source light encounters the static sample (S) 471D, light is thereby emitted by the phosphor reporters contained within the static sample (S) 471D. The emitted light is thereafter directed through an objective lens (OL) 460D into optical fiber 465D to lens (L) 455D, wherein the light is focused and directed to light detecting element (LD) 430D such as a photodiode, avalanched photodiode, photomultiplier tube, photodiode array, or charged coupled device (CCD).

Depending on the detector's 430D spectral response, it may be necessary to provide a filter 436D, such as, but not limited to, spectral filters and spatial filters to filter the excitation light before directing it to the light detecting element (LD) 430D. More specifically, filter 436D is adapted to allow the transmission of emission wavelengths while blocking illumination wavelengths. The signal received from the light detecting element (LD) 430D is then fed into an amplifier 425D for increasing the power of the signal received from the light detecting element (LD) 430D.

The electrical signal output (OP) 475D represents the intensity of light in the emission band which provides the amount of reporter present which is used in quantitation of dilution or other characteristics of the static sample (S) 471D.

Simultaneous detection of multiple markers is possible, at least where the markers have different excitation bands or different emission bands. Where the excitation bands differ, multiple laser diodes emitting at respective appropriate wavelengths are combined using a wavelength division multiplexer or other suitable techniques, such as frequency labeling, frequency modulation, and lock-in detector device. If the emission bands are different (whether or not the excitation bands are different), light in the different emission bands is separated and sent to multiple detectors. If the emission bands overlap, a single detector may be used, but other detection techniques are used. One example is to use time multiplexing techniques so that only one marker is emitting at a given time. Alternatively, the different laser diodes can be modulated at different characteristic frequencies and lock-in detection performed.

The present invention enables the ultrasensitive detection of anti-Stokes phosphors and anti-Stokes organic dyes by exploiting what is essentially the absence of background noise (e.g., autofluorescence, serum/fixative fluorescence, excitation light scatter) that are advantageous characteristics of anti-Stokes markers. Some embodiments of the invention utilize time-gated detection and/or wavelength-gated detection for optimizing detection sensitivity, discriminating multiple samples, and/or detecting multiple probes on a single sample. Phase-sensitive detection can also be used to provide discrimination between signal(s) attributable to an anti-Stokes phosphor and background noise (e.g. autofluorescence) which has a different phase shift.

Referring now to FIG. 5 is shown a depiction of the physical instrumentation configuration utilized in Examples 1-3 below. Specifically, a near infrared (980 nm) laser light source 550 (30 mW) was directed through an IR pass light filter 535 and focused using a glass lens 555 into a fluorescence cell sample 50. Orthogonally, the fluoresced light emitted from the sample was directed through a near IR cutting/block filter 536 and which was then detected by a light detecting element 530 comprising a charged coupled device (CCD) camera. The output 575 from light detection element 530 is routed to a standard personal computer 580. In the preferred embodiment, personal computer 580 is a Pentium class IBM compatible personal computer printing a Microsoft Windows-based operating system.

Example 1

In the configuration of FIG. 5, near infrared (980 µm) laser excitation light source 550 (30 mW) (Phosphor Technology, Ltd, Essex, UK) was passed through an IR pass coloured glass filter 535 (Oriel, Surry, UK, Schott model No RG 830) and focused by a lens 555 into a fluorescence cell sample 50 (1 cm path length) (Hellma GmbH & Co KG, Müllheim, Germany) containing a liquid to which had been added an anti-Stokes marker (e.g., a rare earth oxide obtained from Phosphor Technology, Ltd, Essex, UK, Catalog No. PTIR660) at 0.1% (w/w) concentration. The marker used exhibited a red fluorescence when irradiated at 980 nm in anti-Stokes fluorescence.

The emitted light from the sample passed through a red light filter (~685-695 nm) (e.g., Edmond Optics Ltd, York, UK, Catalog No. C43-089) 536 and was detected by the light detecting element 530, a CCD camera (Astrocam, Cambridge, UK, part No 4201-TE4/A fitted with EEV 05-10 CCD chip 298×1152 pixels 22.5 µm square) and two standard camera lenses mounted front to front (Nikon, Surry, UK, Model Series E 50 mm focal length, 1:1.8).

Separately, the same light source was passed through a cell sample 50 containing the same liquid that did not contain an anti-Stokes marker. No signal was obtained from the unmarked liquid.

Example 2

In the configuration of FIG. 5, a near infrared (980 nm) laser excitation light source 550 (30 mW) (Phosphor Technology, Ltd, Essex, UK) was passed through an IR pass coloured glass filter 535 (Oriel, Surry, UK, Schott model No RG 830) and focused by a lens 555 into a fluorescence cell sample 50 (1 cm path length) (Hellma GmbH & Co KG, Müllheim, Germany) containing a liquid to which had been added an anti-Stokes marker (a rare earth oxide obtained from Phosphor Technology, Ltd, Essex, UK, Catalog No. PTIR545) at 0.1% (w/w) concentration. This marker exhibits a green fluorescence when irradiated at 980 nm in anti-Stokes fluorescence.

The emitted light from the sample 50 passed through a green light filter (~510-590 nm) (Edmond Optics Ltd, York, UK, Catalog No. C46-151) 536 and was detected by the light detecting element 530, a CCD camera (Astrocam, Cambridge, UK, part No 4201-TE4/A fitted with EEV 05-10 CCD chip 298×1152 pixels 22.5 μm square) and two standard camera lenses mounted front to front (Nikon, Surry, UK, Model Series E 50 mm focal length, 1:1.8).

Separately, the same light source was passed through a cell sample 50 containing the same liquid that did not contain an anti-Stokes marker. No signal was obtained from the unmarked liquid.

Example 3

In the configuration of FIG. 5, a near infrared (980 nm) laser excitation light source 550 (30 mW) (Phosphor Technology, Ltd, Essex, UK) was passed through an IR pass coloured glass filter 535 (Oriel, Surry, UK, Schott model No RG 830) and focused by a lens 555 into a fluorescence cell sample 50 (1 cm path length) (Hellma GmbH & Co KG, Müllheim, Germany) containing a liquid to which had been added an anti-Stokes marker (a rare earth oxide obtained from Phosphor Technology, Ltd, Essex, UK, Catalog No. PTIR475) at 0.1% (w/w) concentration. This marker exhibits a blue fluorescence when irradiated at 980 nm in anti-Stokes fluorescence.

The emitted light from the sample 50 passed through a blue light filter (~410-490 nm) (Edmond Optics Ltd, York, UK, Catalog No. C46-149) 536 and was detected by the light detecting element 530, a CCD camera (Astrocam, Cambridge, UK, part No 4201-TE4/A fitted with EEV 05-10 CCD chip 298×1152 pixels 22.5 μm square) and two standard camera lenses mounted front to front (Nikon, Surry, UK, Model Series E 50 mm focal length, 1:1.8).

Separately, the same light source was passed through a cell sample 50 containing the same liquid that did not contain an anti-Stokes marker. No signal was obtained from the unmarked liquid.

Figure 6:
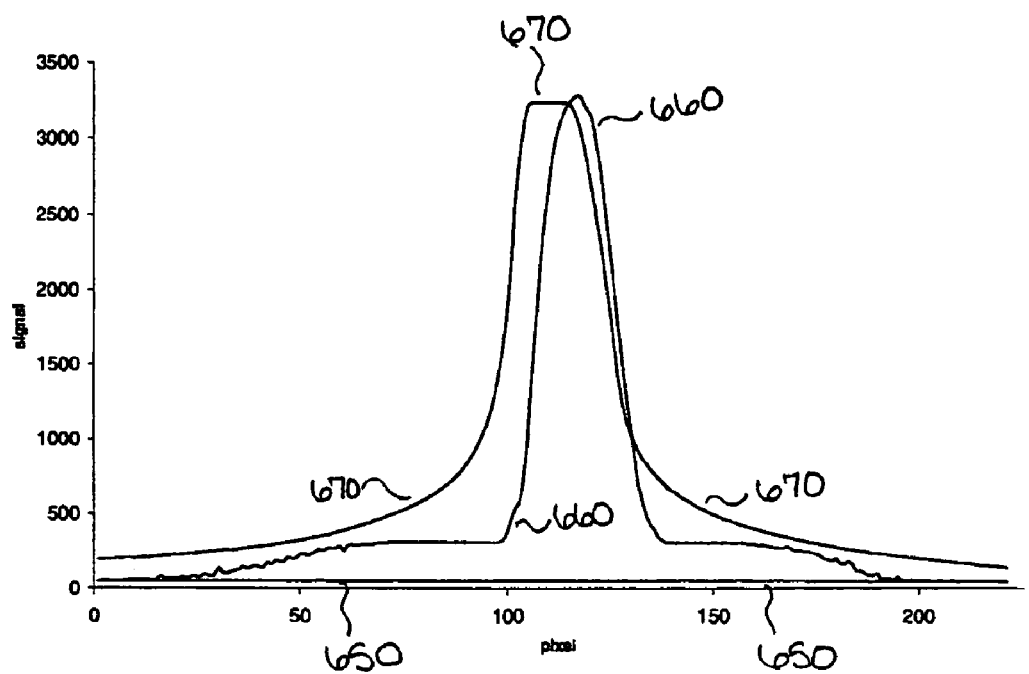
FIG. 6 a graphical depiction of the signal outputs of the samples tested in Examples 1, 2, and 3 utilizing the apparatus configuration of FIG. 5.

Now referring to FIG. 6, a graphical depiction of the samples tested in Examples 1 and 2 above is shown. Specifically, FIG. 6 shows the output signals for the unmarked liquid samples the signal depicted as a generally flat line 250 extending the width of the graph. The output signal of the liquid sample marked with 0.1% blue up-converter of Example 3 is depicted by line 260. Similarly, output signal of the liquid sample marked with 0.1% green up-converter of Example 2 is depicted by line 270. In FIG. 6 the signal of the green up-converter 270 was normalized down to the signal of the blue up-converter 260. The detector was saturated by the signal of the green marker.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method for identifying a liquid comprising the steps of:
   a) adding to the liquid a luminescent compound that absorbs electromagnetic radiation of a first wavelength and emits fluorescent light of a second wavelength which is shorter than the first wavelength, wherein the compound comprises atoms selected from the groups consisting of ytterbium and erbium; ytterbium and thulium ytterbium and holmium; and ytterbium and terbium,
   b) exposing the compound to electromagnetic radiation of the first wavelength; and,
   c) detecting electromagnetic radiation of the second wavelength, thereby identifying the liquid.

2. The method of claim 1, wherein the compound is present in the liquid at a concentration of less than or equal to 10 parts per million.

3. The method of claim 2, wherein the compound is present in the liquid at a concentration of less than or equal to 1 part per million.

4. The method of claim 3, wherein the compound is present in the liquid at a concentration of less than or equal to 0.1 part per million.

5. The method of claim 1, wherein a laser is the source of the electromagnetic radiation of step b).

6. The method of claim 1, wherein in step c) the radiation of the second wavelength is quantified.

7. The method of claim 1, wherein the liquid is selected from the group consisting of a petroleum product, a perfume, water, a beverage, an agrochemical, a bulk liquid, and an additive for fuels or lubricants.

8. The method of claim 7 wherein the liquid is a petroleum product.

9. The method of claim 8 wherein the compound is used to differentiate a petroleum product in a pipeline.

10. The method of claim 1, wherein the wavelength of step b) is 300 nm to 1800 nm.

11. The method of claim 10, wherein the wavelength of step b) is 900 nm to 1100 nm.

12. The method of claim 11, wherein the wavelength of step b) is 960 nm to 985 nm.

13. The method of claim 10, wherein the wavelength of step b) is 1500 nm to 1600 nm.

14. The method of claim 1, wherein the emission of electromagnetic radiation of step c) is within the wavelength range of 300 nm to 1800 nm.

15. The method of claim 14, wherein the emission of electromagnetic radiation of step c) is within the wavelength range of 300 nm to 799 nm.

16. The method of claim 14, wherein the emission of electromagnetic radiation of step c) is within the wavelength range of 800 nm to 1050 nm.

17. The method of claim 1, wherein the liquid contains more than luminescent compound.

18. The method of claim 17, wherein each of the luminescent compounds in the liquid absorbs light of a wavelength or wavelength range that does not overlap that absorbed by any other luminescent compound in the liquid.

19. The method of claim 17 comprising the steps of:
   a) adding two or more luminescent compounds to the liquid;
   b) exposing the liquid to a first electromagnetic radiation of a first wavelength;

c) exposing the liquid to a second electromagnetic radiation of a second wavelength;

d) detecting a first emission of electromagnetic radiation from the liquid at a shorter wavelength than the wavelength of step b); and, e) detecting a second emission of electromagnetic radiation from the liquid at a shorter wavelength than the wavelength of step c), whereby the emissions of steps d) and e) identifies the liquid.

20. The method of claim 19, wherein the first electromagnetic radiation of step d) is within the range of about 300 nm to 1800 nm and the second electromagnetic radiation of step e) is within the range of about 300 nm to 1800 nm, but not within the first electromagnetic radiation.

21. The method of claim 20, wherein the first electromagnetic radiation of step d) is within the range of about 300 nm to 799 nm and the second electromagnetic radiation of step e) is within the range of about 800 nm to 1050 nm.

22. The method of claim 19, wherein the first electromagnetic radiation of step b) is within the range of about 800 nm to 1800 nm and the second electromagnetic radiation of step c) is within the range of about 800 nm to 1800 nm but not within the first electromagnetic radiation.

23. The method of claim 22, wherein the electromagnetic radiation of step b) is within the range of about 900 nm to 1100 nm and the electromagnetic radiation of step c) is within the range of about 1500 nm to 1600 nm.

24. The method of claim 1, wherein the compound is phosphorescent.

25. The method of claim 1, wherein the compound is incorporated into a gel, a particle composite, a vitroceramic matrix, or a polymer.

26. The method of claim 1, wherein the compound is dissolved in the liquid.

27. The method of claim 1, wherein the compound is a particle suspended in the liquid.

28. The method of claim 27, wherein the compound has a particle size diameter of less than or equal to 100 μm.

29. The method of claim 28, wherein the particle size is less than or equal to 10 μm.

30. The method of claim 29, wherein the particle size is less than or equal to 1 μm.

31. The method of claim 30, wherein the particle size is less than or equal to 300 nm.

32. The method of claim 31, wherein the particle size is less than or equal to 100 nm.

33. The method of claim 32, wherein the particle size is less than or equal to 10 nm.

34. The method of claim 27, wherein the particle is monodispersed.

35. The method of claim 27, wherein the particle is polydispersed.

36. The method of claim 27, wherein the particle is colloidal.

37. The method of claim 1, wherein the luminescent compound is bound to a second compound to form a composition.

38. The method of claim 37, further comprising binding the composition to a complementary binding member specific for the composition before exposing the compound to the electromagnetic radiation.

39. The method of claim 38, wherein the complementary binding member comprises a protein.

40. The method of claim 39, wherein the protein is an antibody.

41. The method of claim 38, wherein the complementary binding member comprises a saccharide moiety.

42. The method of claim 38, wherein the complementary binding member comprises a polynucleotide.

43. The method of claim 37, wherein the second compound comprises a polynucleotide.

44. The method of claim 37, wherein the second compound increases the solubility of the luminescent compound in the liquid.

45. The method of claim 44, wherein the second compound comprises a $C_1$ to $C_{24}$ alkyl group and/or a $C_6$ to $C_{30}$ aryl group, each of which can be substituted with from 1 to 6 hydroxy, $C_1$ to $C_6$ ether, $C_3$ to $C_{24}$ polyether, thio, $C_1$ to $C_6$ thioether, amino, $C_1$ to $C_6$ alkylamino, $C_2$ to $C_{12}$ dialkylamino, nitro, carboxy, carboxy-$C_1$ to $C_6$-alkyl, sulfoxy, carboxamido, carbox-$C_1$ to $C_6$-alkylamido, $C_1$ to $C_6$ alkylamido, $C_6$ to $C_{18}$ arylamido, $C_1$ to $C_6$ alkarylamido, $C_1$ to $C_6$ alkylimido, $C_1$ to $C_6$ alkylhydrazido, or $C_6$ to $C_{18}$ arylhydrazido groups.

46. The method of claim 1, the liquid further comprising additives to increase the solubility of the compound in the liquid.

47. The method of claim 37, wherein the second compound enhances the dispersion of the luminescent compound in the liquid.

48. The method of claim 47, wherein the second compound comprises a $C_1$ to $C_{24}$ alkyl group and/or a $C_6$ to $C_{30}$ aryl group, each of which is optionally substituted with from 1 to 6 hydroxy, $C_1$ to $C_6$ ether, $C_3$ to $C_{24}$ polyether, thio, $C_1$ to $C_6$ thioether, amino, $C_1$ to $C_6$ alkylamino, $C_2$ to $C_{12}$ dialkylamino, nitro, carboxy, carboxy-$C_1$ to $C_6$-alkyl, sulfoxy, carboxamido, carbox-$C_1$ to $C_6$-alkylamido, $C_1$ to $C_6$ alkylamido, $C_6$ to $C_{18}$ arylamido, $C_1$ to $C_6$ alkarylamido, $C_1$ to $C_6$ alkylimido, $C_1$ to $C_6$ alkylhydrazido, or $C_6$ to $C_{18}$ arylhydrazido groups.

49. The method of claim 47, wherein the second compound is a surfactant.

50. The method of claim 1, wherein the compound is an organic dye.

* * * * *